US010518104B2

(12) United States Patent
Boll et al.

(10) Patent No.: US 10,518,104 B2
(45) Date of Patent: Dec. 31, 2019

(54) SYSTEMS AND METHODS OF UNATTENDED TREATMENT

(71) Applicant: Cynosure, LLC, Westford, MA (US)

(72) Inventors: James Boll, Auburndale, MA (US); Rafael Armando Sierra, Westford, MA (US); Elizabeth Kneen, Somerville, MA (US); Allan Cameron, South Natick, MA (US); Adrian Mark West, Newton, MA (US); Kevin Young, Needham, MA (US); Bo Chen, Mountain View, CA (US)

(73) Assignee: CYNOSURE, LLC, Westford, MA (US)

( * ) Notice: Subject to any disclaimer, the term of this patent is extended or adjusted under 35 U.S.C. 154(b) by 200 days.

(21) Appl. No.: 15/138,020

(22) Filed: Apr. 25, 2016

(65) Prior Publication Data
US 2016/0310756 A1 Oct. 27, 2016

Related U.S. Application Data

(60) Provisional application No. 62/321,141, filed on Apr. 11, 2016, provisional application No. 62/210,967, (Continued)

(51) Int. Cl.
*A61N 5/06* (2006.01)
*A61N 5/067* (2006.01)
*A61N 5/00* (2006.01)

(52) U.S. Cl.
CPC .......... *A61N 5/0616* (2013.01); *A61N 5/0625* (2013.01); *A61N 2005/005* (2013.01); (Continued)

(58) Field of Classification Search
CPC ...... A61N 5/06; A61N 5/0613; A61N 5/0616; A61N 5/0625; A61N 2005/063; (Continued)

(56) References Cited

U.S. PATENT DOCUMENTS 5,029,581 A  7/1991 Kaga et al.
5,327,886 A * 7/1994 Chiu ..................... A61F 7/007
601/15

(Continued)

FOREIGN PATENT DOCUMENTS

CN      204815398 U    7/2015
EP      2110159        10/2009
(Continued)

OTHER PUBLICATIONS

International Search Report and Written Opinion for International application No. PCT/US2017/027067 mailed from the International Search Authority dated Sep. 4, 2017 (17 pages).
(Continued)

*Primary Examiner* — Ahmed M Farah
(74) *Attorney, Agent, or Firm* — K&L Gates LLP

(57) ABSTRACT

In accordance with various aspects of the present teachings, systems and methods for applying treatment energy, e.g., electromagnetic radiation such as laser radiation in the visible and near infrared wavelengths, to body areas having bulges and fat deposits, loose skin, pain, acne and/or wounds. In some aspects, the systems and methods can enable relatively lengthy treatments to be performed by having the practitioner set-up and/or start the treatment, thereafter allowing the treatment to proceed safely and effectively without the continued presence of the practitioner.

13 Claims, 18 Drawing Sheets

Related U.S. Application Data filed on Aug. 27, 2015, provisional application No. 62/151,894, filed on Apr. 23, 2015.

(52) U.S. Cl.
CPC .. *A61N 2005/063* (2013.01); *A61N 2005/067* (2013.01); *A61N 2005/0632* (2013.01); *A61N 2005/0643* (2013.01); *A61N 2005/0647* (2013.01); *A61N 2005/0659* (2013.01); *A61N 2005/0662* (2013.01)

(58) Field of Classification Search
CPC .... A61N 2005/0632; A61N 2005/0633; A61N 2005/0635; A61N 2005/0643; A61N 2005/0645; A61N 2005/0647; A61N 2005/065
USPC ........ 607/88–91, 96, 100; 606/9, 10, 13, 17; 128/898
See application file for complete search history.

(56) References Cited

U.S. PATENT DOCUMENTS

| | | | |
|---|---|---|---|
| 6,080,146 A | 6/2000 | Altshuler et al. | |
| 6,126,294 A | 10/2000 | Koyama et al. | |
| 6,277,085 B1* | 8/2001 | Flynn ................ | A61H 23/0218 601/78 |
| 6,508,813 B1 | 1/2003 | Altshuler | |
| 6,517,532 B1 | 2/2003 | Altshuler et al. | |
| 6,653,618 B2 | 11/2003 | Zenzie | |
| 6,663,620 B2 | 12/2003 | Altshuler et al. | |
| 6,878,144 B2 | 4/2005 | Altshuler et al. | |
| 6,974,451 B2 | 12/2005 | Altshuler et al. | |
| 6,976,985 B2 | 12/2005 | Altshuler et al. | |
| 6,997,923 B2 | 2/2006 | Anderson et al. | |
| 7,351,252 B2 | 4/2008 | Altshuler et al. | |
| 7,540,869 B2 | 6/2009 | Altshuler et al. | |
| 7,586,957 B2 | 9/2009 | Sierra et al. | |
| 7,763,016 B2 | 7/2010 | Altshuler et al. | |
| 7,856,985 B2 | 12/2010 | Mirkov et al. | |
| 7,929,579 B2 | 4/2011 | Hohm et al. | |
| 3,002,768 A1 | 8/2011 | Altshuler et al. | |
| 8,265,446 B2 | 9/2012 | Lonero et al. | |
| 8,317,779 B2 | 11/2012 | Mirkov et al. | |
| RE43,881 E | 12/2012 | Baranov et al. | |
| 8,322,348 B2 | 12/2012 | Mirkov et al. | |
| 8,328,794 B2 | 12/2012 | Altshuler et al. | |
| 8,328,796 B2 | 12/2012 | Altshuler et al. | |
| 8,915,948 B2 | 12/2014 | Altshuler et al. | |
| 9,028,536 B2 | 5/2015 | Sierra et al. | |
| 9,326,910 B2* | 5/2016 | Eckhouse ............. | A61H 7/008 |
| 9,358,152 B2* | 6/2016 | Baxter .................. | A61F 7/10 |
| 2004/0260210 A1* | 12/2004 | Ella ..................... | A61H 7/008 601/7 |
| 2005/0197681 A1* | 9/2005 | Barolet ................ | A61B 18/203 607/86 |
| 2005/0215988 A1* | 9/2005 | Altshuler ............. | A61B 18/203 606/9 |
| 2006/0004306 A1* | 1/2006 | Altshuler ............. | A61B 18/203 601/3 |
| 2007/0179570 A1* | 8/2007 | De Taboada ......... | A61H 7/006 607/88 |
| 2007/0208326 A1* | 9/2007 | Connors .............. | A61B 18/203 606/9 |
| 2007/0270785 A1* | 11/2007 | Jones ................... | A61B 18/203 606/9 |
| 2008/0086187 A1* | 4/2008 | Baxter .................. | A61F 7/10 607/108 |
| 2009/0054880 A1 | 2/2009 | Aharon | |
| 2010/0204762 A1 | 8/2010 | De Taboada et al. | |
| 2012/0116271 A1* | 5/2012 | Caruso ................. | A61B 18/203 601/6 |
| 2012/0150079 A1* | 6/2012 | Rosenberg ............ | A61H 7/003 601/6 |
| 2013/0178764 A1 | 7/2013 | Eckhouse et al. | |
| 2014/0194957 A1 | 7/2014 | Rubinfeld et al. | |
| 2014/0350643 A1 | 11/2014 | Pepitone et al. | |
| 2015/0045675 A1 | 2/2015 | Chernomorsky | |
| 2016/0158575 A1 | 6/2016 | Levatter | |
| 2016/0287333 A1 | 10/2016 | Morrison | |
| 2017/0266426 A1 | 9/2017 | Ha et al. | |

FOREIGN PATENT DOCUMENTS

| | | |
|---|---|---|
| KR | 100353164 | 11/1999 |
| KR | 200660031262 | 10/2004 |
| KR | 20160014740 | 1/2016 |
| KR | 101906514 | 5/2017 |
| WO | 2010100540 | 9/2010 |
| WO | 2017180663 | 10/2017 |

OTHER PUBLICATIONS

"VelaShape II: Cellulite Treatment & body Contouring", Candela, 2011 (8 pages).

Screen captures from YouTube video clip entitled "Nubway Model (NBW-I323)", 11 pages, published on Aug. 25, 2015. Video is from Beijing Nubway S & T Co., Ltd. Retrieved from Internet: <https://www.youtube.com/watch?v=NcY4P7aWVbs>.

Screen captures from YouTube video clip entitled "Cryolipolysis Fat Freezing Machine", 11 pages, published on Nov. 6, 2015, Cryolipolysis Machine for sale. Retrieved from Internet: <https://www.youtube.com/watch?=9d_QLIr9LHE>.

Office Action in corresponding U.S. Appl. No. 16/231,336, dated Jul. 3, 2019 (18 pages).

Office Action in corresponding U.S. Appl. No. 16/231,351 dated Jun. 18, 2019.

* cited by examiner

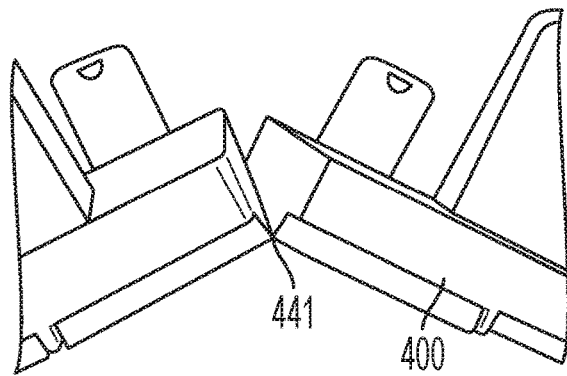
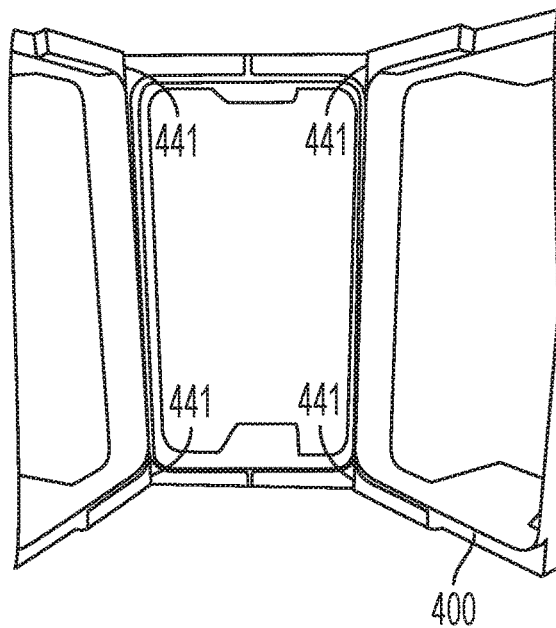
FIG. 9A   FIG. 9B
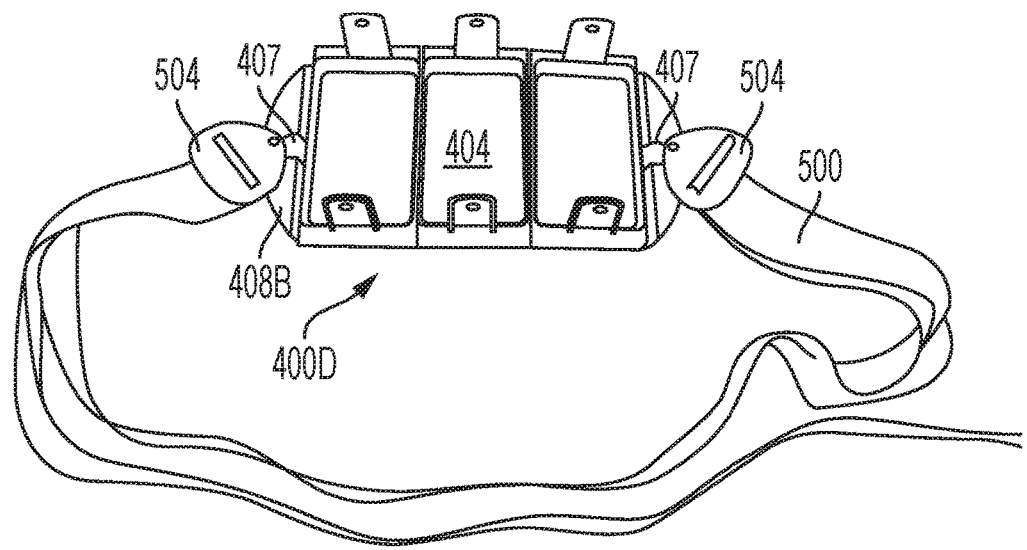
FIG. 10 ized Photothermolysis (SPTL), has been widely used for various photothermal therapies, such as hair removal and superficial vascular treatment. The objective of SPTL is to choose an energy source, e.g., laser light, having a specific wavelength that is selectively or preferentially absorbed by the targeted tissue (such as adipocytes and lipid bilayer structures), with less absorption and therefore less thermal effect on the surrounding tissues (such as epidermis). Optimal SPTL is achieved when the targeted tissue has a much higher energy absorption compared to other surrounding tissues. Frequently, this effect is controlled by selecting lasers having particular wavelengths for specific cosmetic purposes. But in certain procedures, selection of wavelength alone is not itself sufficient to create a large enough energy absorption differential between target and non-target tissues to achieve optimal therapeutic effects without some degree of damage to surrounding non-target tissues. Approaches that increase the energy absorption differential and control heating at the treatment site while lessening collateral damage of non-target tissues can in some aspects involve modulating the radiation exposure through pulsed applications of laser light. For example, in accordance with various aspects of the present teachings, the methods and systems can utilize a near infrared laser having a wavelength within the range of 1064 nm that is selected based on its tissue penetrance and the relatively low absorption of the EMR by the major chromophores in the skin (e.g., melanin and water). Exemplary power densities are from about 0.5 to about 10 W/cm$^2$, or
SYSTEMS AND METHODS OF UNATTENDED TREATMENT

FIELD

The present disclosure relates generally to systems and methods for applying energy (e.g., electromagnetic radiation such as laser radiation in the visible and near infrared wavelengths) to treat, for example, body areas having bulges and fat deposits, loose skin, pain, acne and/or wounds.

BACKGROUND

The benefits of being able to raise and/or lower the temperature in a selected region of tissue for various therapeutic and cosmetic purposes has been known for some time. For instance, heated pads or plates or various forms of electromagnetic radiation, including microwave radiation, electricity, infrared radiation and ultrasound have previously been used for heating subdermal muscles, ligaments, bones and the like to, for example, increase blood flow, to otherwise promote the healing of various injuries and other damage, and for various therapeutic purposes, such as frostbite or hyperthermia treatment, treatment of poor blood circulation, physical therapy, stimulation of collagen, cellulite treatment, adrenergic stimulation, wound healing, psoriasis treatment, body reshaping, non-invasive wrinkle removal, etc. Heating may be applied over a small localized area, over a larger area, for example to the hands or feet, or over larger regions of tissue, including the entire body.

While optical and near infrared (NIR) radiation (collectively referred to hereinafter as "optical radiation") is generally both less expensive, and being non-mutagenic, safer than microwave radiation, the use of optical radiation has heretofore not been considered suitable for most applications involving heating of tissue at depth, the term "tissue at depth" as used herein meaning tissue at the border zone of the dermis and hypodermis, some of which tissue may be in the lower dermis, mostly at a depth deeper than 1 mm, and tissue below this border zone to a depth of up to about 50 mm. The reason why optical radiation has not been considered suitable is because such radiation is both highly scattered and highly absorbed in surface layers of tissue, precluding significant portions of such radiation from reaching the tissue regions at depth to cause heating thereof. In view of the energy losses due to scattering and absorption, substantial optical (including NIR) energy must be applied in order for enough such energy to reach a region of tissues at depth to have a desired effect. However, such high energy can cause damage to the surface layers of tissue, making it difficult to achieve desired photothermal treatments in tissue regions at depth. For these reasons, optical radiation has had limited value for therapeutic and cosmetic treatments on tissue at depth.

SUMMARY

In order to enable photothermal treatment of tissue regions at depth (e.g., hyperthermic treatment of fatty tissue), various aspects of the present teachings provide methods and systems for modulating the application of radiation (or modulating the intensity of the radiation applied to the tissue) over an extended treatment time. By way of non-liming example, the photothermal treatment of fatty tissue can raise the mean tissue temperature at a treatment site at depth above about 40° C., e.g., from about 40° C. to about 48° C., or from about 42° C. to about 46° C. by applying laser irradiation to the treatment site to maintain this supraphysiological temperature (greater than 37° C.) at the treatment site over a relatively extended period of time (e.g., a few minutes to hours depending on the particular temperature applied). In some aspects, for example, the treatment radiation can be applied over a relatively long duration (e.g., from about 3 to about 50 minutes, or from about 10 to about 45 minutes, or from about 15 to about 35 minutes, or about 25 minutes) to achieve the desired depth of treatment, thereby heating fatty tissue to trigger heat-induced injury that causes the adipocytes to undergo apoptosis or lipolysis. The residual cellular debris is gradually removed by the body through inflammation and the resultant immune system clearing process, which can take weeks to months depending on the extent of injury at the site. Since the regeneration process of adipose tissue is very slow (over years), the total volume of fat within the treatment area decreases due to loss of adipocytes that would otherwise act as storage units for fat.

Since the techniques described above involve applying treatment energy through the patient's skin surface, peak temperatures generally occur at or near the patient's skin surface and decrease, sometimes significantly, with depth. Notably, 46° C. or 48° C. is not the upper limit of treatment, as higher temperatures (47-50° C. or more e.g. 60° C., 70° C., 80° C., etc.) can also be effective to denature cells and ablate tissue, but these likewise raise the mean heat level in the non-target tissues and possibly cause collateral damage. Because it is desirable to confine the hyperthermic treatment to the target tissue while keeping temperatures of dermal tissue above the targeted tissue at depth below injury threshold (i.e., lower than about 46-47° C.), the electromagnetic treatment parameters (such as radiation pattern, fluence, exposure time, etc.) can be modulated over the extended treatment time, and in some aspects by taking into account the cooling rate on the skin surface, an optimized temperature profile/gradient in the target tissue can be achieved during the treatment.

One exemplary technique, called Selective Photothermolysis (SPTL), has been widely used for various photothermal therapies, such as hair removal and superficial vascular treatment. The objective of SPTL is to choose an energy source, e.g., laser light, having a specific wavelength that is selectively or preferentially absorbed by the targeted tissue (such as adipocytes and lipid bilayer structures), with less absorption and therefore less thermal effect on the surrounding tissues (such as epidermis). Optimal SPTL is achieved when the targeted tissue has a much higher energy absorption compared to other surrounding tissues. Frequently, this effect is controlled by selecting lasers having particular wavelengths for specific cosmetic purposes. But in certain procedures, selection of wavelength alone is not itself sufficient to create a large enough energy absorption differential between target and non-target tissues to achieve optimal therapeutic effects without some degree of damage to surrounding non-target tissues. Approaches that increase the energy absorption differential and control heating at the treatment site while lessening collateral damage of non-target tissues can in some aspects involve modulating the radiation exposure through pulsed applications of laser light. For example, in accordance with various aspects of the present teachings, the methods and systems can utilize a near infrared laser having a wavelength within the range of 1064 nm that is selected based on its tissue penetrance and the relatively low absorption of the EMR by the major chromophores in the skin (e.g., melanin and water). Exemplary power densities are from about 0.5 to about 10 W/cm$^2$, or from about 4 to about 6 W/cm², and a particularly useful range is about 0.9 to about 1.4 W/cm². Alternatively, suitable systems can utilize a wavelength within the range of about 800 nm to about 1300 nm, selected based on tissue penetrance, and power densities from about 0.5 to about 10 W/cm², or from about 4 to about 6 W/cm², and a particularly useful range is about 0.9 to about 1.4 W/cm². To maintain an appropriate hyperthermic temperature range in the target tissue (e.g., about 40-47° C. in the fat layer) while avoiding pain and other unwanted side effects related to overheating, the laser can be modulated such that it can be pulsed so as to generate an on/off pattern or by modulating the intensity of the laser (e.g., between a high intensity and low intensity), which causes the temperature to cycle within the appropriate hyperthermic temperature range, as disclosed for example in U.S. Pub No. 20080103565 entitled "Method and Apparatus for Treatment of Cutaneous and Subcutaneous Conditions" and U.S. Pub. No. 20070213792 entitled "Treatment of Tissue Volume with Radiant Energy," the teachings of which are incorporated by reference in their entireties. With the laser on (or at a desired relatively high intensity), the temperature can rise to the upper limits of the desired range. A periodic pause in radiation (or a lowering of the intensity) permits temperatures in the target site (and non-target site) to drop. Optionally, cooling (especially of the upper non-target tissue) can be further enhanced by using external devices (e.g., contact cooling), while laser radiation can resume (or its intensity is increased) before the target tissue temperature drops below the appropriate hyperthermic temperature range. In some embodiments, radiation is delivered through the contact cooled surface, which continuously cools. Alternatively, contact cooling is modulated via pulse on and off in concert with the delivery of radiation. The pulses can be repeated for the duration of the treatment (e.g., from about 3 minutes to about 2 hours, from about 5 minutes to about 45 minutes, from about 15 minutes to about 35 minutes, or about 25 minutes).

With such extended treatment times, it may also be desirable that at least some, if not all, of the treatment can be accomplished hands-free and/or at times by the practitioner. By way of example, a hands free system in accordance with various aspects of the present teachings could enable the practitioner to start treatment of a first patient with a first system, and allow the practitioner to attend to or treat a second subject during the first subject's relatively long treatment time. In various aspects, such a substantially unattended approach can reduce the costs associated with treatment by freeing up the practitioner's time and potentially enable a less skilled practitioner to be able to conduct a majority of the treatment. For example, a less skilled practitioner can check in with and talk to the patient, to get a sense of the patient's comfort and then call in a more skilled practitioner to adjust the treatment parameters if necessary. In accordance with some aspects of the present teachings, the systems and methods for relatively hands-free and/or substantially unattended treatment described herein can provide treatment that is reliable, safe, and/or relatively comfortable to the patient over the length of the treatment time. In addition, various aspects of the systems and methods disclosed enable customization so as to fit various body areas requiring treatment and/or the isolation of the target treatment area.

In accordance with various exemplary aspects of the present teachings, a system for substantially unattended treatment of body tissue is provided, the system comprising a housing and at least one source of electromagnetic radiation for generating treatment energy contained within the housing. The system also comprises a plurality of applicators, with each of the applicators being adapted to be placed in proximity to a treatment region of tissue of a patient's body and comprising an optical window having a skin-contacting surface through which the treatment energy is transmitted from the applicator to the treatment region. A plurality of umbilical cords, each of which extends from the housing to a distal end coupled to one of the plurality of applicators, defines a conduit through which treatment energy generated by the at least one electromagnetic radiation source is delivered from the housing to the applicator (e.g., through at least one optical waveguide extending through the conduit). The system can also comprise a frame configured to be coupled to the patient's body in a fixed position relative to the treatment region and defining at least one aperture into which a surface of the treatment region can extend. The frame and at least one applicator can be coupled to one another in a variety of manners, but are generally removably coupled such that at least a portion of the skin-contacting surface of the optical window is disposed in contact with at least a portion of the surface of the treatment region extending into the aperture upon coupling the applicator with the frame. In some aspects, for example, the frame and the applicator can comprise complementary mating features for removably coupling the applicator to the frame. By way of example, the frame can comprise a snap-fit coupling mechanism for removably coupling the applicator to the frame. In various aspects, the system can additionally comprise an adjustable belt configured to be coupled to the frame for securing the frame to the patient's body.

In some aspects, the housing can comprise at least one arm extending from the housing for supporting the umbilical cords. For example, the arm can extend from the housing so as to be disposed above the patient's body when performing treatment so as to maintain secure contact between the skin-contacting surface of the applicator and the portion of the surface of the treatment region extending into the aperture of the frame. In various aspects, the housing can be maneuverable (e.g., it can include wheels to position the housing and the umbilical cords extending therefrom in a desired position) and/or the arm(s) can be adjustable so as to alter its orientation relative to the patient. In some exemplary aspects, the arm can additionally comprise at least one brake (e.g., a roller brake) in contact with the plurality of umbilical cords so as to maintain the umbilical cords at a desired position relative to the patient. By way of example, the at least one brake can limit movement of the umbilical cords when performing treatment so as to facilitate secure contact between the skin-contacting surface of the applicator and the portion of the surface of the treatment region extending into the aperture of the frame when coupled to the applicator. Additionally or alternatively, the brake can enable a desired amount of lead of the umbilical cord to be maintained between the brake and the applicator at the distal end of the umbilical cord. Moreover, each umbilical cord can be associated with its own brake such that the desired lead for each umbilical cord can be adjusted individually.

In various aspects, the frame can define a plurality of apertures, each of which can isolate a portion of a target treatment region. Additionally or alternatively, two or more frames can be used to isolate portions of the target treatment region. In various aspects, the frame can be configured to be simultaneously coupled with two or more of the plurality of applicators such that the skin-contacting surface of each of the applicators is disposed in contact with the portion of the surface of the treatment region extending into one of the apertures. In such aspects, for example, the frame can comprise a hinge disposed between adjacent apertures such that the orientation of the apertures can be adjusted relative to each other (e.g., upon tightening a belt coupled to the frame about a portion of the subject's body).

In various aspect, the system can further comprise a cooling mechanism configured to cool the skin-contacting surface of the applicators when performing treatment. By way of non-limiting example, a fluid pathway can extend through the conduit for circulating cooling fluid between the housing and the applicator via the umbilical cord.

Additionally, in some aspects, each of the applicators can comprise a contact sensor to determine whether the skin-contacting surface of the optical window is disposed in contact with the surface of the treatment region.

In various aspects of the present teachings, the system can comprise at least one mask configured to be coupled to the frame and configured to occlude the aperture of the frame so as to prevent a portion of the surface of the patient's body from extending into the aperture and into contact with the optical window of the applicator. It will be appreciated in light of the present teachings that the mask can also be coupled to a cooling mechanism for cooling the mask during treatment. In some aspects, the mask can define an unmasked portion having an area smaller than each of the optical window of the applicator and the aperture of the frame associated with the mask, with each of the applicators comprising a contact sensor to determine whether the skin-contacting surface of the optical window is disposed in contact with the surface of the treatment region extending through the unmasked portion. Additionally or alternatively, at least one of the size and shape of the unmasked portion can be adjustable, for example, so as to customize the tissue to which the treatment energy is applied. To increase patient comfort during the procedure, for example, in some aspects the frame can comprise a skin-contacting surface disposed about the at least one aperture, wherein the skin-contacting surface of the frame is contoured to fit the area of the patient undergoing treatment. By way of example, the skin-contacting surface can be curved or non-planar so as to accommodate the submental region of a patient.

In accordance with various exemplary aspects of the present teachings, a method for treating body tissue is provided, the method comprising coupling a frame to a patient's body in a fixed position relative to a treatment region of tissue, the frame defining at least one aperture into which a surface of the treatment region extends. At least one applicator can be coupled to the frame, each applicator comprising an optical window having a skin-contacting surface through which treatment energy is configured to be transmitted from the applicator to the treatment region, wherein at least a portion of the skin-contacting surface of the optical window is disposed in contact with at least a portion of the surface of the treatment region extending into said aperture upon coupling with the frame. Thereafter, treatment energy can be transmitted to the portion of the surface of the treatment region extending through the aperture of the frame and disposed in contact with the skin-contacting surface of the optical window, the treatment energy being generated by at least one source of electromagnetic radiation disposed in a housing and delivered to the applicator via an umbilical cord extending from the housing to a distal end of the umbilical cord that is coupled to the applicator. In some aspects, coupling at least one applicator to the frame can comprise coupling a plurality of applicators to the frame, wherein each of the applicators is associated with a different umbilical cord and a different aperture of the frame configured to isolate a different surface of the treatment region.

In various aspects, the housing can additionally comprise at least one arm extending from the housing for supporting the umbilical cords, the method further comprising disposing the arm above the patient's body when performing treatment. In some exemplary aspects, the arm can also comprise at least one brake in contact with each of the plurality of umbilical cords so as to maintain a desired amount of lead of each umbilical cord between the at least one brake and the applicator associated with each umbilical cord.

In some exemplary aspects, coupling the frame to the patient's body can comprise securing a belt coupled to the frame around at least a portion of the patient's body. By way of example, when the treatment region comprises one of submental, jowl, and neck tissue, the belt can be secured about the patient's head and/or neck. Alternatively, when the treatment region comprises abdominal tissue, the flanks, the under-bra area (in the back or in the front), the belt can be secured about the patient's torso. Finally, when the treatment region comprises tissue of the patient's arm or leg (e.g., where the thighs meet and/or the saddle bag area), for example, the belt can be secured around the patient's arm or leg, respectively. In various related aspects, the frame can comprise a hinge disposed between adjacent apertures, wherein coupling the frame to the patient's body further comprises adjusting the orientation of the apertures relative to each other (e.g., as the belt is tightened about the patient).

In various aspects, the method can also include coupling the frame to at least one mask configured to occlude a portion of the frame's aperture so as to prevent a portion of the surface of the patient's body from extending into the aperture and into contact with the optical window of the applicator. The unmasked portion of the mask can have an area smaller than each of the optical window of the applicator and the aperture of the frame associated with the mask, the method further comprising adjusting at least one of the size and shape of the unmasked portion (e.g., so as to customize the tissue to which the treatment energy is applied).

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

FIGS. 9A-B depict additional detail of an exemplary frame for use in accordance with various aspects of the present teachings, the frame having a hinge disposed between the apertures for adjusting the orientation of the apertures when the frame is secured to the patient.

FIG. 10 depicts another exemplary frame having three apertures coupled to a belt for securing the frame about a portion of the patient's body.

DETAILED DESCRIPTION

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicant's teachings in any manner.

In accordance with various aspects of the present teachings, systems and methods for providing photothermal treatment of tissue at depth are provided herein. In light of the extended treatment times typically utilized to perform such treatments, various aspects of the present teachings provide systems and methods for a reliable, safe, and/or relatively comfortable photothermal treatment to the patient in a manner that is relatively hands-free and/or with relatively little oversight, thereby potentially reducing the costs associated with continued oversight by the practitioner. In addition, various aspects of the systems and methods disclosed enable customization so as to fit various body areas requiring treatment and/or the isolation of the target treatment area.

Figure 1:
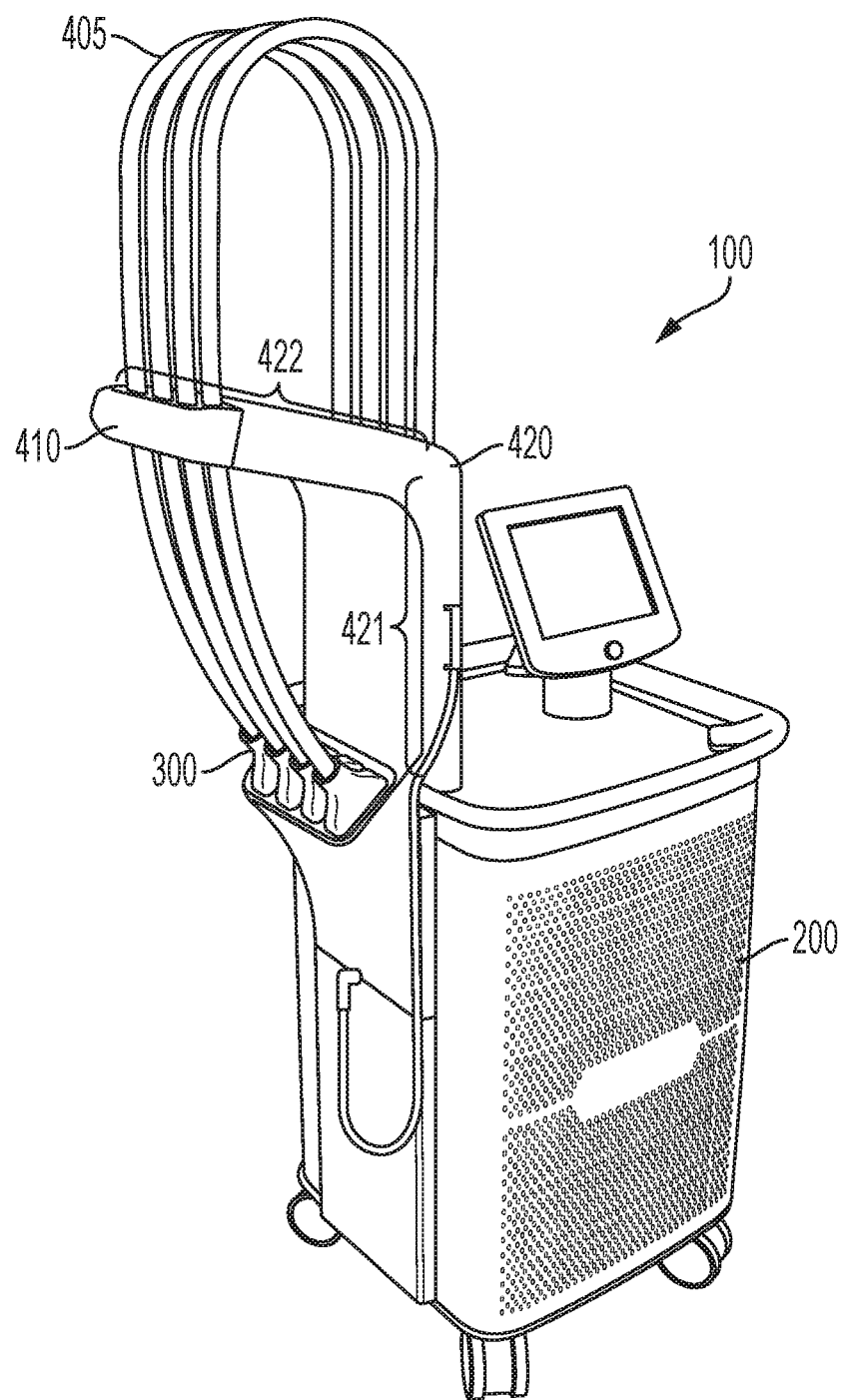
FIG. 1 shows an exemplary system for providing photothermal treatment of a target region of a patient's body in accordance with various aspects of the present teachings. As shown, the system includes a housing, a plurality of umbilical cords extending therefrom that are supported by an arm, and an applicator disposed at the distal end of each umbilical cord.
Figure 2:
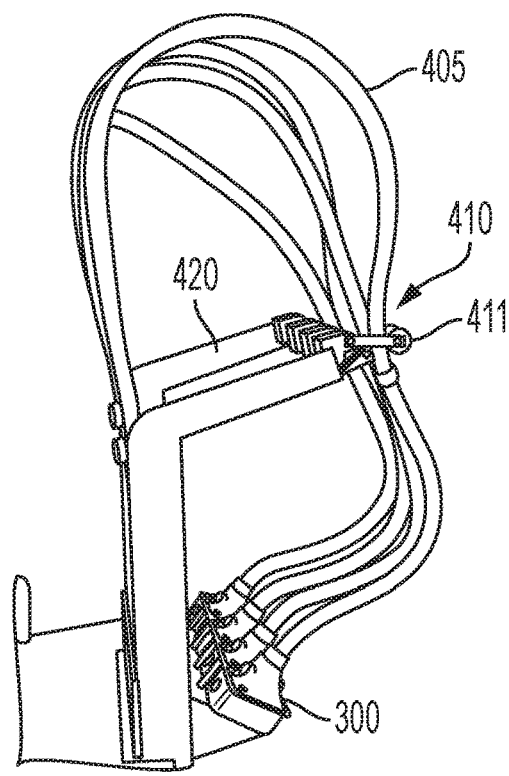
FIG. 2 shows a view of the system of FIG. 1 depicting the arm in additional detail. As shown, the arm includes a brake mechanism associated with each umbilical cord to assist in controlling the positioning and/or securement of the applicator. The housing additionally include a dock for storing the applicators when not in use.
Figure 3:
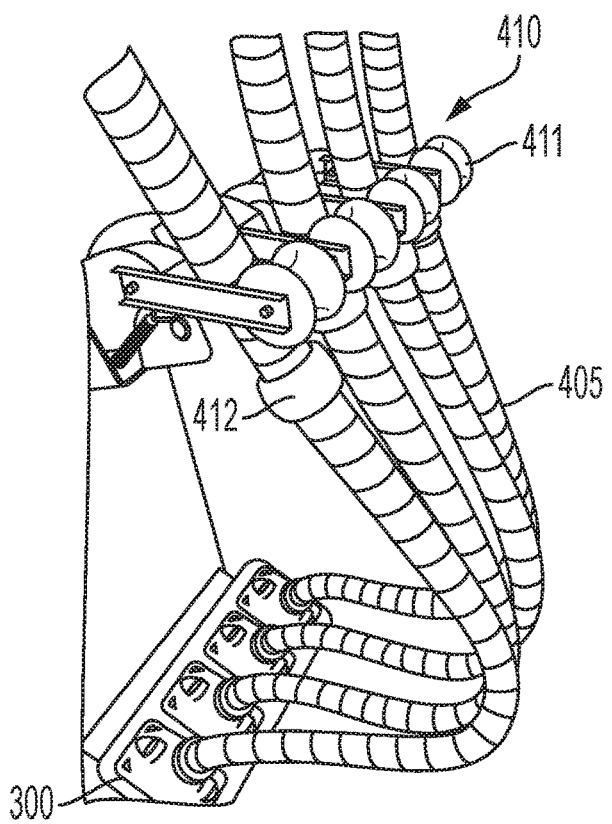
FIG. 3 depicts another view of the system of FIG. 1 showing the exemplary brake mechanism in additional detail.
Figure 4:
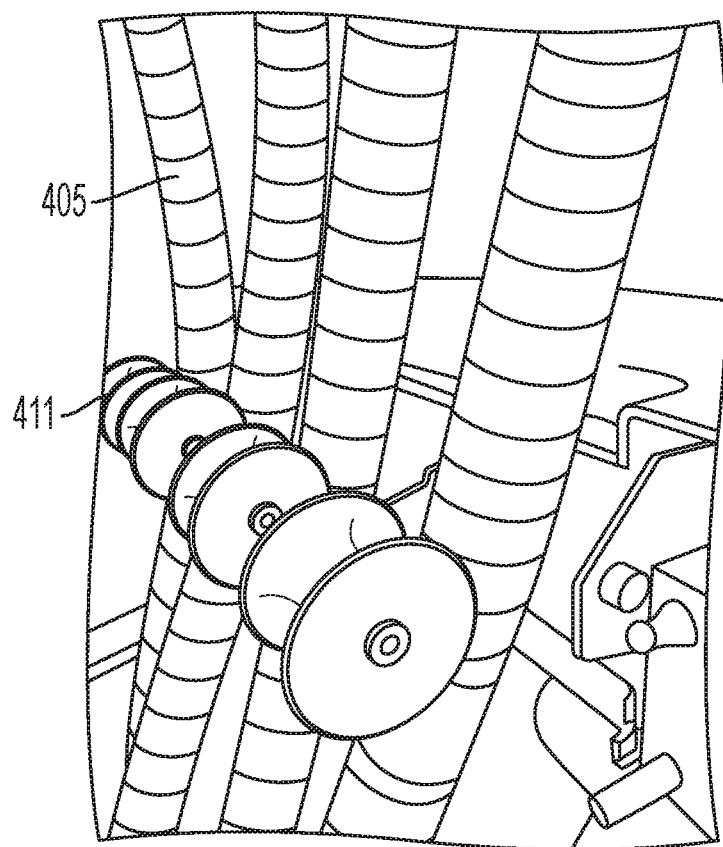
FIG. 4 depicts a close up of the exemplary brake mechanism.

Referring now to FIG. 1, an exemplary system 100 in accordance with various aspects of the present teachings is depicted. As shown, system 100 provides for the non-invasive (or less-invasive) photothermal treatment for fat reduction. Though the treatment is typically described with respect to the treatment of undesired body fat by the application of electromagnetic radiation to the fatty tissue through the external surface of the skin, it will nonetheless be appreciated by a person skilled that the systems and methods described herein can be utilized to provide any number of photothermal treatments known in the art and modified in accordance with the present teachings including the treatment of loose skin, pain, acne and/or wounds, all by way of non-limiting example. Exemplary approaches to photothermal treatment of tissue at depth and modified for use in accordance with methods and systems of the present teachings are disclosed, for example, in U.S. Pub. No. 20070213792 entitled "Treatment of Tissue Volume with Radiant Energy,"; U.S. Pub No. 20080103565 entitled "Method and Apparatus for Treatment of Cutaneous and Subcutaneous Conditions"; U.S. Patent Pub. No. 20140025033 entitled "Non-Invasive Fat Reduction by Hyperthermic Treatment"; U.S. Pat. No. 7,276,058 entitled "Method and Apparatus of Treatment of Cutaneous and Subcutaneous Conditions" issued on Oct. 2, 2007; U.S. Pat. No. 7,351,252 entitled "Method and Apparatus for Photothermal Treatment of Tissue at Depth" issued on Apr. 1, 2008; and U.S. Pat. No. 8,915,948 entitled "Method and Apparatus for Photothermal Treatment of Tissue at Depth" issued on Dec. 23, 2014, the teachings of which are incorporated by reference in their entireties.

As shown in FIG. 1, the exemplary system 100 for the non-invasive treatment of undesired body fat generally includes a housing 200 that can contain one or more sources of electromagnetic radiation (not shown), a plurality of umbilical cords 405 extending therefrom, and one or more applicators 300 coupled to the distal end of the umbilical cords 405 for applying the treatment radiation to the patient's skin when disposed in contact with the surface of the treatment region. Though the depicted exemplary system includes four applicators, any of a number of applicators 300 can be included in the system, for example, one applicator, two applicators, four applicators, or more. When not in use, the plurality of applicators 300 can be stored in a dock on the housing 200. Suitable energy sources can be, for example, temperature control (e.g., cooling and/or heating), light based energy sources, electromagnetic radiation, RF energy, and ultrasound energy, as known in the art and modified in accordance with the present teachings. As discussed in detail below, the treatment energy generated by the EMR source(s) can be delivered to the applicator, for example, via an optical waveguide (e.g., optical fiber) coupled to the EMR source(s) and extending through the umbilical cord 405.

As shown in FIGS. 1-4, the system 100 additionally comprises an arm 420 extending from the housing 200 that can support at least a portion of the umbilical cords 405, for example, above the subject to be treated and/or at a desired distance from the patient and/or other portions of the system including, for example, the housing 200 containing the energy source. The arm 420 can extend upward and outward from the housing in a variety of manners so as to support the umbilical cords 405 about or relative to the patient. As shown for example, the arm 420 includes a substantially vertical portion 421 extending from an upper surface of the housing 200 and a substantially horizontal portion 422 that extends from the top of the substantially vertical portion 421. The lengths of the vertical portion 421 and horizontal portion 422 can be fixed or can be adjustable in order to obtain proper positioning of the umbilical cords relative to the patient. By way of example, the arm 420 can include an adjustment mechanism (e.g., a telescoping portion hinge, pivot, or gimbaled mount) to adjust the length or angular orientation of one or more portions of the arm 420. In some aspects, the substantially vertical portion 421 of the arm 420 can have a height, for example, that is a function of the desired length (e.g., lead) of the umbilical 405 including, for example, a height in a range from about 8 inches to about 48 inches, from about 10 inches to about 36 inches, or about 12 inches. Likewise, the substantially horizontal portion 422 of the arm 420 can extend about 3 inches to about 36 inches, from about 9 inches to about 24 inches, or about 12 inches from the substantially vertical portion 421 such that the brake mechanism 410 (discussed in detail below) maintains the umbilical cords 405 at a distance of about 12 to 20 inches from the substantially vertical portion 421 of the arm 420 and/or from the housing 200.

As noted above and best shown in FIGS. 3 and 4, the arm 420 can also include a brake mechanism 410 for allowing the desired amount of lead from each of the plurality of umbilical cords 405 to be drawn toward the subject being treated and/or to help ensure that the umbilical cords 405 (and optionally additional umbilical lead) are at the desired position selected by the user. Though the exemplary system 100 is shown to include opposing roller brakes 441 disposed at the distal most end of the arms 420 as discussed in detail below, it will be appreciated that opposing roller brakes 411 is merely one approach to holding the plurality of umbilical cords 405 with some lead at a height above where the subject will be treated. Rather, it will be appreciated in light of the present teachings that any of a number of brake mechanisms can be employed for hold the umbilical cord 405 (and optionally, additional umbilical lead) at a desired position (e.g., height and/or distance) from the patient.

As noted above, the brake mechanism 410 comprises opposing roller brakes 411 between which the umbilical cords 405 extend and which apply a frictional or compression force to the cord 405 when disposed therebetween. In this manner, the roller brakes 411 can enable additional lead of the umbilical cord 405 to be pulled (e.g., with some resistance) toward the subject such that the skin-contacting surface of the applicator 300 attached to the umbilical cord 405 can sit with good contact on the skin surface of the patient. As otherwise discussed herein, the resistance and tension of the brake mechanism 410 enables the practitioner to tailor the amount of lead in each umbilical cord 405 for each respective applicator 300 in view of how to effectively place each applicator 300 into a frame 400 so that the contact surface of the applicator 300 is able to contact the subject's skin surface through the aperture 404 of the frame to ensure desired contact with the skin contact surface of the applicator 300 and the skin surface of the patient.

In various aspects, a self-retraction and positioning feature can also be built into the umbilical cord 405. By way of example, a spring can be disposed within a portion of the umbilical cord 405 (commonly referred to as a whip), that enables automatic retraction of the umbilical cord 405. After a user has completed use of the applicator 300 and unfastens the applicator 300 from the frame 400, for example, the user may simply push the umbilical cord 405 upward toward the brake mechanism 410 with a single hand. As a result the umbilical cord 405 can return to its initial position (e.g., as defined by stop 412 having a larger diameter than the umbilical cord 405) by a single handed movement of the user, with the stop 412 being positioned to allow the applicator 300 to be seated in its dock.

Figure 5:
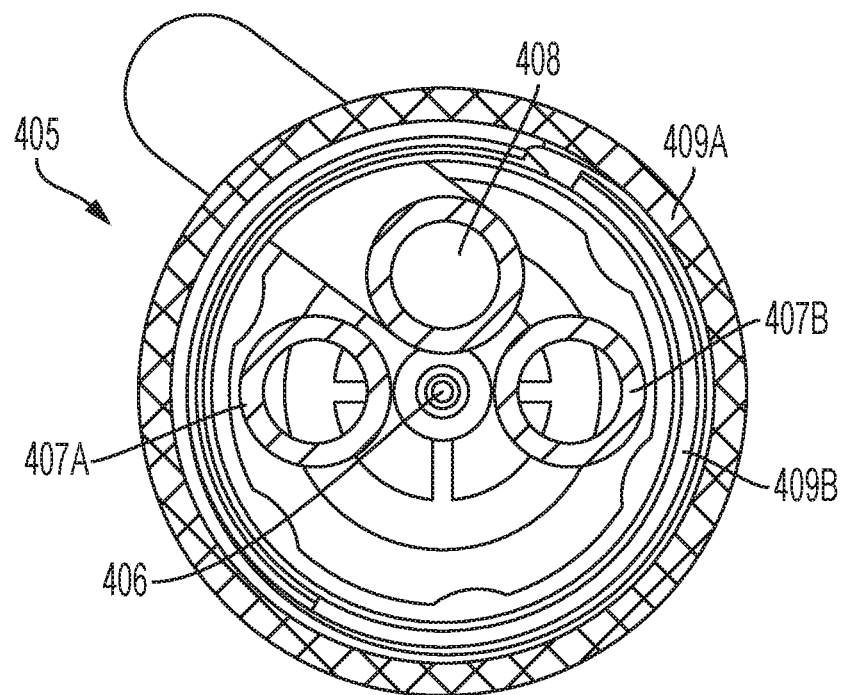
FIG. 5 schematically depicts a cross-section of an exemplary umbilical cord for use in the system of FIG. 1.

It will be appreciated that umbilical cords 405 for use in accordance with the present teachings can have a variety of configurations but generally define a conduit therethrough and are sufficiently flexible such that they can be maneuvered into a desired position. By way of example, as shown in FIG. 5, the exemplary umbilical cord 405 comprises a corrugated, flexible outer surface 409A (e.g., made of plastic) as well as a corrugated, inner shell 409B that is also flexible but can be made of a material (e.g., metal, stainless steel) that provides increased protection to the fibers and/or conduit extending through the conduit defined by the umbilical cord 405. For example, FIG. 5 depicts that an optical waveguide (e.g., optical 406) extends through the conduit for delivering EMR from the EMR sources to the applicators. Additionally, as discussed in detail below, one or more fluid pathways 407A,B can extend through the conduit, for example, for delivering cooling fluid to and returning cooling fluid from the applicator 300. Additionally, one or more signal cables 408 can be provided to enable electric communication between the housing 200 and the applicator 300 (e.g., including for transmitting signals generated by contact sensors of the applicators).

Figure 6:
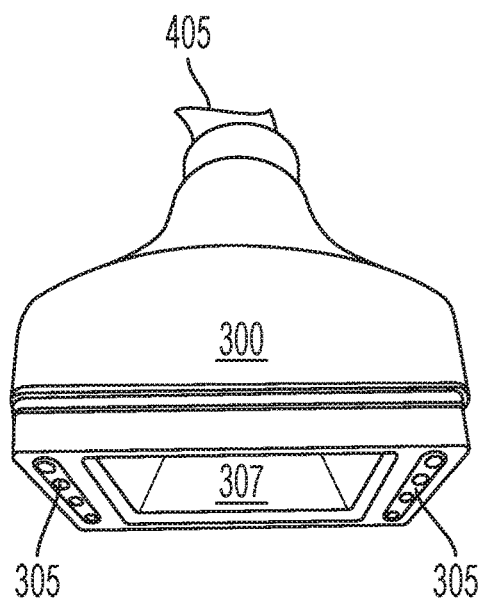
FIG. 6 depicts additional detail of the applicator of FIG. 1.

Referring now to FIG. 6, the exemplary applicator 300 of FIG. 1 is depicted in additional detail. As shown in FIG. 6, the applicator 300 (or treatment head) is coupled to the umbilical cord 405 (e.g., for delivery of the treatment energy) and includes an optical window having a skin-contacting surface 307 through which the treatment energy is transmitted from the applicator 300 to the treatment region. The optical window can have a variety of configurations but generally comprises a material (e.g., glass, sapphire) selected to provide good optical coupling with the skin when in contact therewith. It will also be appreciated that the contact surface 307 of the applicator 300 can have a variety of sizes and shapes (e.g., depending on the surface to be treated) including rectangular, square, triangular, circular, oval, ellipse, trapezoid, rhombus, pentagon, hexagon, octagon, or parallelogram, all by way of non-limiting example. As shown in FIG. 5, for example, the contact surface is rectangular, and can have a short side that ranges from about 1 cm to about 10 cm and a long side that range from about 2 cm to about 15 cm. In one exemplary embodiment, the short side measures 3 cm and the long side measures 5 cm. In another exemplary embodiment, the short side measures 4 cm and the long side measured 6 cm. In various aspects, the contact surface 307 can cover an area that ranges from about 2 $cm^2$ to about 150 $cm^2$, or about 15 $cm^2$, or about 24 $cm^2$.

With continued reference to FIG. 6, the applicator 300 also includes a plurality of contact sensors 305 (e.g., eight contact sensors) that ensure contact with the skin surface during treatment. In one embodiment, when there is incomplete contact or an absence of contact with one of the contact sensors 305 with the skin surface, the system takes action to avoid injury. For example, when incomplete contact or an absence of contact is detected, a controller in the system 100 will turn off the energy delivered to the applicator 300, thereby inhibiting radiation transmission through the skin contact surface 307 of the applicator 300. In another embodiment, when incomplete or an absence of contact is detected, by one or more of the contact sensors 305, the system 100 will lower the amount of energy (e.g., the intensity) delivered to the applicator 300 from the radiation source. Any of a number of suitable contact sensors 305 may be employed, for example, an electrical contact sensor (e.g., an electrical resistance sensor, an electrical impedance sensor, a capacitance sensor), a pressure contact sensor (e.g., a mechanical sensor). In various aspects, the use of contact sensors can be valuable in that it preserves eye safety. Suitable approaches to ensuring contact between the treatment head and the patient's skin and modified for use in accordance with methods and systems of the present teachings are disclosed, for example, in U.S. Pub. No. 20060149343 entitled "Cooling System For a Photocosmetic Device" and U.S. Pat. No. 6,653,618 entitled "Contact Detecting Method and Apparatus for an Optical Radiation Handpiece" issued Nov. 25, 2003, the teachings of which are incorporated by reference in their entireties.

As noted above, it may also be desirable to cool the skin-contacting surface 307 of the applicator 300 so as to cool the layers of the skin above the target region at depth. In some aspects, for example, as discussed above with reference to FIG. 5, one or more fluid pathways 407A, B can extend through the conduit, for example, for delivering cooling fluid to the applicator 300 for maintaining the skin-contacting surface and/or the skin surface at a desired temperature (e.g., to confine the hyperthermic treatment to the target tissue while keeping temperatures of dermal tissue above the targeted tissue at depth below injury threshold). Additionally, where the applicator surface is cooled, the use of contact sensors prevents unwanted heating (e.g., in the epidermal and/or dermal layer) due to lack of contact and/or incomplete contact between the skin surface and the cooled applicator surface. Suitable approaches to cooling the skin during photothermal treatment and modified for use in accordance with methods and systems of the present teachings are disclosed, for example, in U.S. Pat. No. 6,517,532 entitled "Light Energy Delivery Head" issued on Feb. 11, 2003; U.S. Pat. No. 6,663,620 entitled "Light Energy Deliver Head" issued on Dec. 16, 2003; U.S. Pat. No. 6,653,618 entitled "Contact Detecting Method and Apparatus for an Optical Radiation Handpiece" issued Nov. 25, 2003; U.S. Pat. No. 6,974,451 entitled "Light Energy Delivery Head" issued on Dec. 13, 2005; U.S. Pat. No. 6,976,985 entitled "Light Energy Delivery Head" issued on Dec. 30, 2005; U.S. Pat. No. 7,351,252 entitled "Method and Apparatus for Photothermal Treatment of Tissue at Depth" issued on Apr. 1, 2008; U.S. Pat. No. 7,763,016 entitled "Light Energy Delivery Head" issued on Jul. 27, 2010; U.S. Pat. No. 8,002,768 entitled "Light Energy Delivery Head" issued on Aug. 23, 2011; U.S. Pat. No. 8,915,948 entitled "Method and Apparatus for Photothermal Treatment of Tissue at Depth" issued on Dec. 23, 2014; U.S. Pub No. 20080103565 entitled "Method and Apparatus for Treatment of Cutaneous and Subcutaneous Conditions"; U.S. Pub. No. 20070213792 entitled "Treatment of Tissue Volume with Radiant Energy"; and U.S. Pub. No. 20140025033 entitled "Non-Invasive Fat Reduction by Hyperthermic Treatment," the teachings of which are incorporated by reference in their entireties.

As noted above, a self-retracting mechanism can be included with the umbilical cords that can assist in automatic retraction of the umbilical cord 405 and applicator 300 after a user has completed use of the applicator 300. In various related aspects, the applicator can weigh about 0.75 lbs, or from about 0.1 lb to about 10 lbs, or from about 0.25 lbs to about 5 lbs, or from about 0.5 lbs to about 1.5 lbs, by way of non-limiting example. Each applicator together with the umbilical cord can weigh about 3.5 lbs, or from about 0.75 lbs to about 15 lbs, or from about 1.5 lbs to about 7 lbs, or from about 2.5 lbs to about 5 lbs, by way of non-limiting example.

Figure 7A:
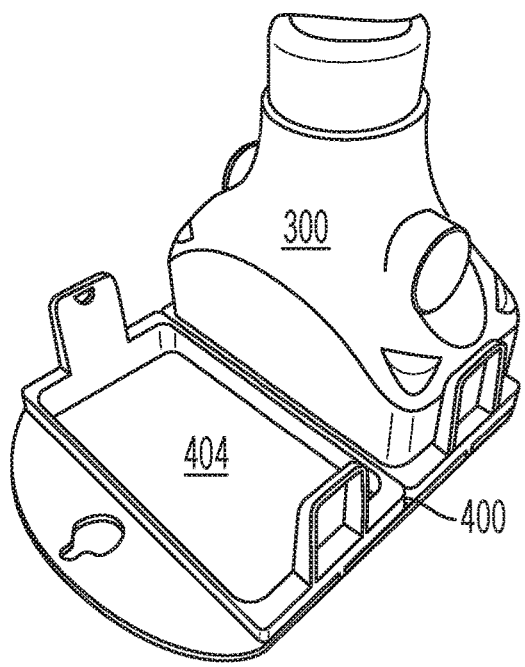
FIG. 7A-C depict the applicator of FIG. 6 coupled to an exemplary frame having at least two apertures that can be secured to the patient in accordance with various aspects of the present teachings.
Figure 7B:
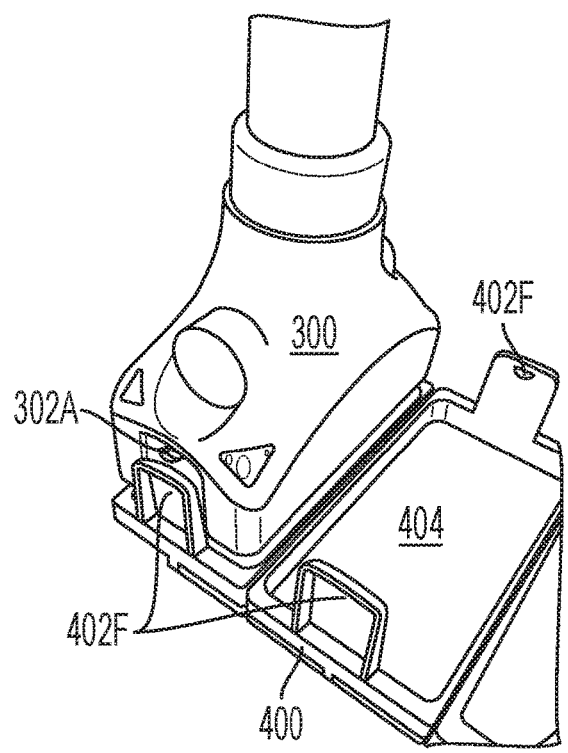
Figure 7C:
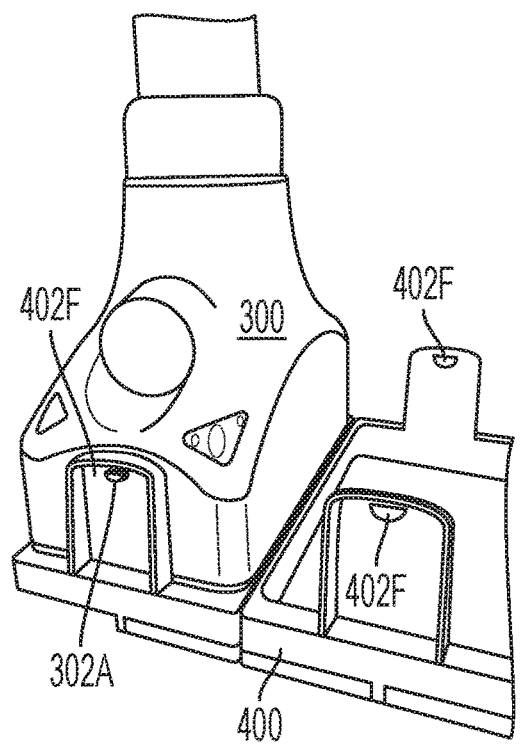

With reference now to FIGS. 7A-C, the applicator 300 is depicted as being removably attached to a frame, which as otherwise discussed herein can be secured to the patient to isolate a treatment region and/or help ensure contact between the skin-contacting surface 307 of the applicator 300 and a portion of the surface of the patient's skin tissue. As shown in FIG. 7A, the applicator 300 is mechanically attached to a frame 400 having an applicator surface and a skin contact surface, and defining two apertures 404 therebetween. FIG. 7A depicts how the applicator 300 is attached at the applicator surface to one of the two apertures 404 of frame 400, with the skin-contacting surface 307 of the applicator 300 (as shown in FIG. 6A) contacting the subject's skin through the aperture 404 of the frame 400. It will be appreciated that the applicator 300 and the frame 400 can be removably coupled using any coupling mechanism known in the art and modified in accordance with the present teachings. By way of example, FIGS. 7B and 7C depict an applicator 300 attaching to a frame 400 through the interaction between a male connector 302A on the applicator 300 that snap fits with a complementary female connector 402F on the applicator attachment side of the frame 400. Other exemplary fastening systems for removably coupling the applicator to the frame include tension fit, clamp, clip, hook and eye, clothespin, buckle, bungee, or zip tie, all by way of non-limiting example.

Figure 8:
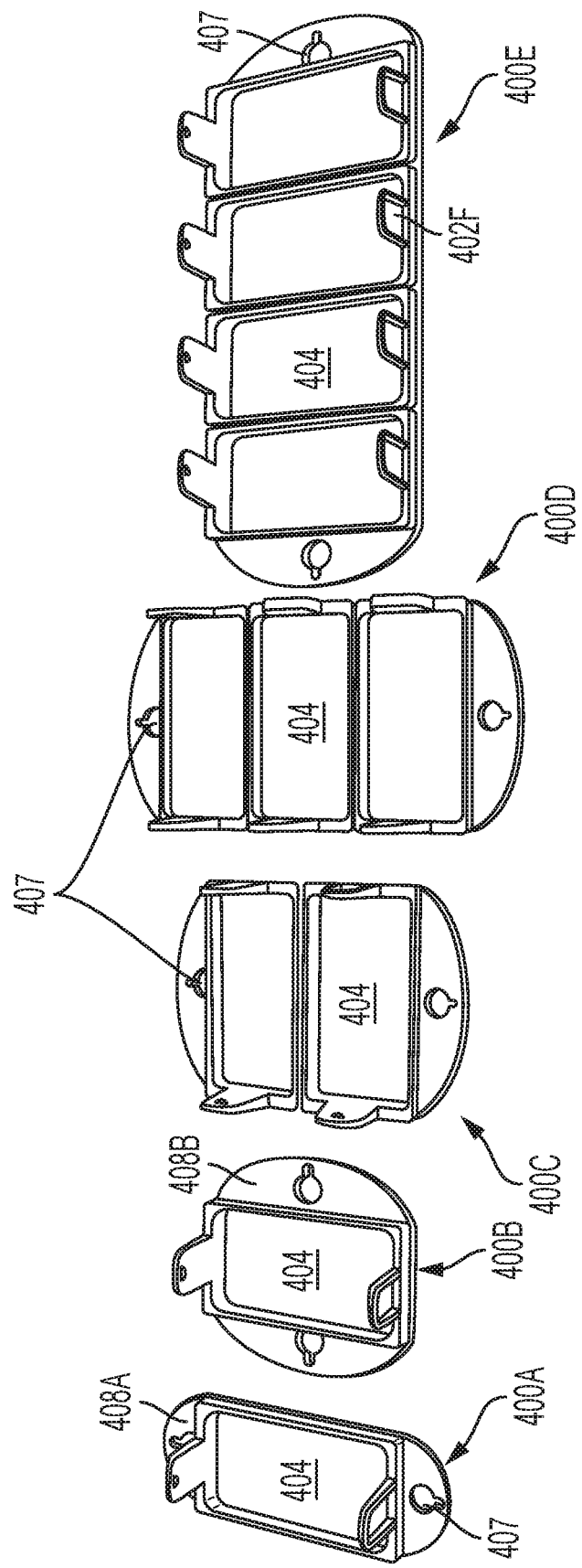
FIG. 8 depicts a variety of exemplary frame configurations that can be employed in the system of FIG. 1.

Additional details of exemplary frames in accordance with various aspects of the present teachings will now be discussed in more detail. With reference now to FIG. 8, a number of exemplary frames 400 that may be employed with the system of FIG. 1 are depicted. As shown in FIG. 8, frames 400A and 400B each have a single aperture 404, frame 400C has two apertures 404, frame 400D has three apertures 404, and frame 400E has four apertures 404, with each of the apertures 404 of the frames 400A-E being associated with a coupling mechanism (e.g., female connectors) on the applicator side of the frame for removably coupling with an applicator 300 (e.g., via snap fit connection). Additionally, as shown each of the frames 400A-E comprises tabs 408A/B that can be utilized to couple to a belt (e.g., through one or more belt loops 407 extending through the tabs 408A/B). It will be appreciated in light of the present teachings that the number of apertures 404, the shape of the apertures (e.g., rectangle, square, circle, hexagon, triangle, etc.), the layout of the apertures (linear pattern of apertures, brick pattern of apertures, vertically stacked column of apertures, or horizontally stacked row of apertures), and the size of the apertures can be customized for the desired treatment area. By way of example, where the region for treatment is contoured (e.g., around the waist of the subject) a frame having multiple hinged apertures may be used to enable treatment of the contour of the body area. In one embodiment, each aperture/applicator treats an area of from about 5 cm$^2$ to about 200 cm$^2$, or from about 10 cm$^2$ to about 150 cm$^2$, or from about 25 cm$^2$ to about 100 cm$^2$.

With reference now to FIGS. 9A-B, an exemplary frame 400 is shown in additional detail in which a hinge 441 is disposed between portions of frame 400 so as to adjust the angular orientation of the adjacent apertures and/or change their proximity to one another. FIG. 9B shows the skin contact side of the frame 400 and the regions where the apertures of the frame 400F are attached to one another via the plurality of hinges 441. For example, one or more hinges can attach adjacent frame portions to one another such that a first aperture of frame 400 is adjacent a second aperture of frame 400. In one embodiment, the hinges 441 are disposed on the skin contact side of the frame 400. The hinges 441 enable the frame 400 to follow the contour of the subject's body, e.g., by articulating the curvature of the area to be treated. In one embodiment, the hinge 441 can be sized to minimize separation between adjacent apertures so that when treatment occurs using a frame having multiple apertures, the treatment is relatively consistent in the overall treatment area despite the distance between adjacent apertures.

Figure 11:
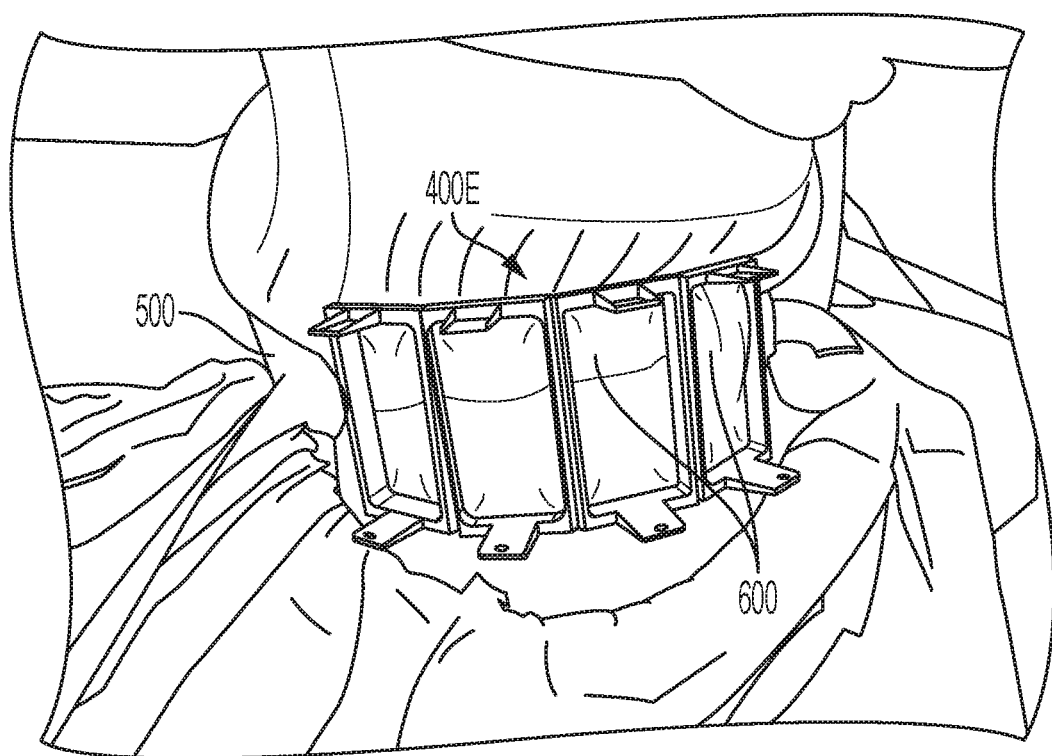
FIG. 11 depicts another exemplary frame having four apertures secured to a patient's body via a belt disposed about the patient's torso, thereby isolating the region(s) for treatment with the applicator(s).

As noted above, the frame can be secured to the patient, for example, prior to removably coupling the applicator to the frame. With reference now to FIG. 10, for example, the system 100 can include a belt 500 having an attachment mechanism (e.g., buckles 504) that attach to the frame 400D via belt loops 407 extending through the tabs 408B disposed on the frame 400D. FIG. 11, for example, depicts the belt 500 tightening a hinged frame 400E having four apertures around the contour of a subject's body, thereby isolating within the four apertures of the frame a skin surface of the treatment region(s) 600 that extend (e.g., bulge) into each aperture of the frame 400D.

Figure 12:
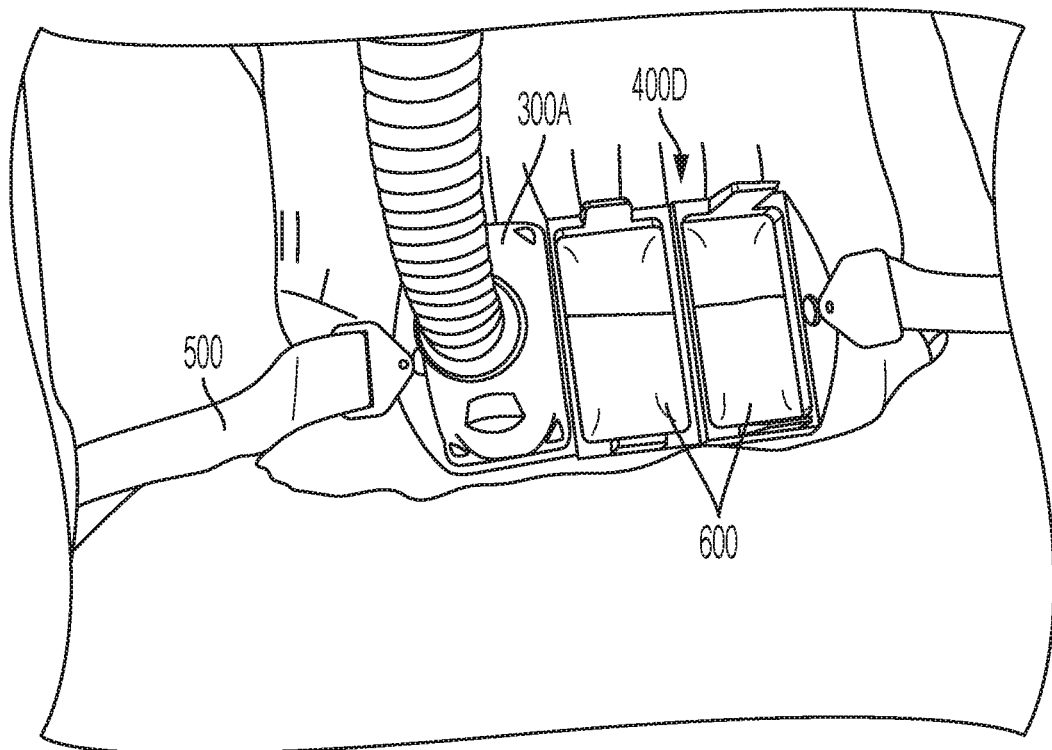
FIG. 12 depicts the exemplary frame of FIG. 10, secured to a patient's body via a belt disposed about the patient's torso, with one applicator being coupled to the frame so as to treat the treatment region within one of the three apertures.

FIG. 12 also shows a belt 500 tightening a hinged frame 400D having three apertures around the circumference of a subject's body thereby isolating the region(s) for treatment 600 with the applicator(s). As shown, the skin contact surface of the coupled applicator 300A is placed in contact with an isolated treatment region 600 having a bulge that is present in the aperture of the frame 400D. Referring still to FIG. 12, with the frame secured to the patient thusly, one or more applicators (e.g., up to four in the case of FIG. 11) can then be coupled to the frame 400D so that the skin-contacting surface 307 of each applicator 300 contacts the skin bulges 600 through each aperture 404 in the frame 400D. For example, the applicators 300 can be fastened to the frame 400D by snapping the male connectors on each applicator 300 with the complementary female connectors on the frame 400D associated with each aperture 404. The bulge of tissue through the aperture and the snap fit connection between the applicator and the frame 400D ensure contact of the skin-contacting surface of the applicator with the surface of the skin tissue 600 that has bulged through the aperture. Optionally, lotion can be disposed on the surface of the isolated region of skin tissue in the aperture 600 prior to coupling the applicator (e.g., via snap fit placement) to the frame and even prior to positioning the frame on the body area to be treated. Suitable lotions can include, for example, baby oil or Palomar® lux lotion. Optionally, contact sensors disposed on the skin contact side of the applicator(s) avoid treatment of the skin tissue when good contact is not in place. In this way, with a cooled applicator skin contact surface, proper cooling of the skin tissue by the applicator is provided and excessive heat treatment (e.g., burns) are avoided.

Figure 13A:
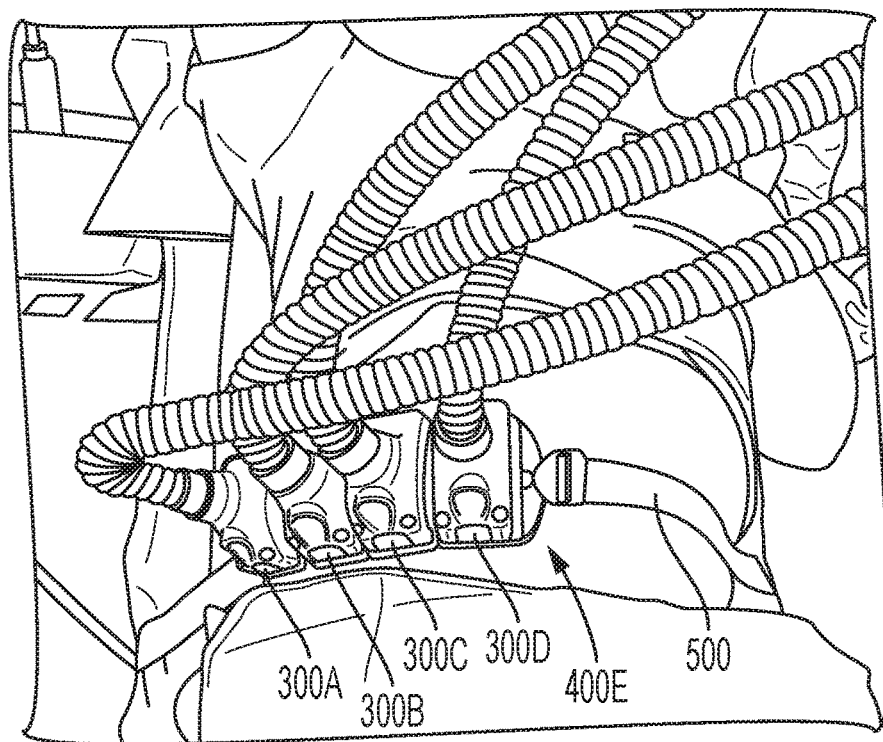
FIG. 13A depicts the exemplary frame of FIG. 11, secured to a patient's body via a belt disposed about the patient's torso, with four applicators being coupled to the frame so as to treat the treatment region within each of the frame's four apertures.

With reference now to FIG. 13A, treatment of a subject with the system shown in FIG. 1 is depicted in which four applicators 300A, 300B, 300C, and 300D are coupled to frame 400E. As shown, the frame 400E is tightened onto the subject via a belt 500 looped around the contours of subject's body so as to treat the regions of a body area isolated by the skin bulges present in the four apertures 404 of the frame 400E. In accordance with various aspects of the present teachings, the umbilical cords are looped through the arm and the brake mechanism that introduce the applicator to the frame with a tension level that ensures good contact between the skin contacting surface of the applicator and the subject's skin tissue. Each applicator is held by its respective umbilical and the umbilical is held from the arm of the system at a distance away from the energy source and at a height to help ensure good contact between the skin contacting surface of the applicator and the subject's skin tissue. Moreover, as discussed above, the applicator is attached to the frame by a removable coupling mechanism such as a snap fit engagement. The tissue isolated within and bulging in the apertures of the frame helps ensure that there is good contact between the skin contact surface of the applicator and the subject's skin tissue. Finally, optional lotion and optional contact sensors on the skin contact surface of the applicator enable the system to be used to treat tissue only when contact (e.g., good contact and/or full contact) is present between the applicator surface and the skin surface.

Figure 13B:
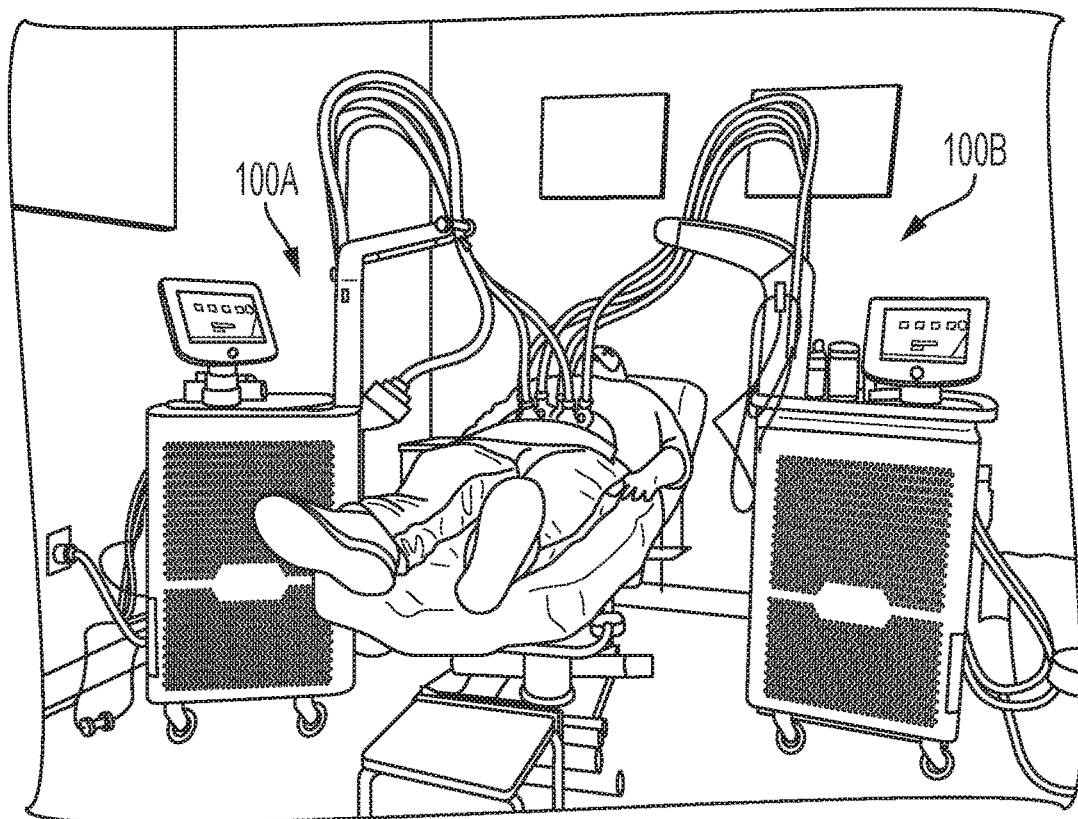
FIG. 13B depicts two exemplary systems shown in FIG. 1, with four applicators from one of the systems and two applicators from the other system being utilized to treat a body area isolated by six apertures of multiple frames that are tightened onto the subject via a belt looped around the subject's body.

As discussed otherwise herein, in this manner the subject can be "set up" for treatment by the practitioner and then require minimal to no additional direct contact with or attention from the practitioner until the treatment time is completed (e.g., for from about 5 minutes to about 2 hours) such that a safe, reliable, comfortable, non-invasive treatment of fat tissue can be achieved while requiring minimal practitioner time considering the length of time required to complete the treatment. FIG. 13B demonstrates how the subject can be positioned relative to the system 100 in accordance with various aspects of the present teachings. As shown, the subject can be disposed (e.g., lie) under the arm to enable the applicator attached to the umbilical to be aided by gravity from each umbilical that is held within the arm by opposing roller brakes. Referring still to FIG. 13B, the subject is treated with two separate systems 100A, 100B using four applicators from one system 100B and two applicators from the other system 100A to treat an abdominal body area isolated by six apertures of multiple frames. In one embodiment, for example, two or more separate frames can be attached to one another via a link (e.g., a "c" shaped loop, substantially "o" shaped loop that has an opening in it that enables frames to be linked together, or one or more snap fit connectors for connecting two or more frames to one another). The frames can be tightened onto the subject via a belt looped around the subject's body. Here regions of a body area isolated by the six separate skin bulges present in six apertures of at least two linked frames are tightened onto the subject via a belt looped around the contours of subject's body.

Additionally, the subject can be in the standing position when the area for treatment is isolated by the belt/frame combination and thereafter sit down or lie down for treatment with the system. By isolating the body area to be treated when the subject is in the position where the appearance of the body area is of most concern, the subject can be certain that his needs are being addressed and further the level of expertise to enable the treatment area to be isolated is lessened versus other treatment modalities. By isolating the treatment area in the frames while the subject is standing and prior to treatment, the subject can comfortably sit, recline, and or lay down during his treatment while knowing that the areas of concern are being addressed by the treatment.

It will be appreciated in light of the present teachings, that the systems and methods described herein can be customized or configured to treat specific treatment regions. For example, in addition to the abdominal treatments depicted in FIGS. 13A-B, a subject may have concern about other areas on the torso like the flanks, tissue below the bra area (on the front or back), also, areas of arms or legs, or about the appearance of fat and fullness in the face, chin, and neck area, by way of non-limiting examples. With specific reference to the submental area, the jowls, and the neck, these visible areas may be of concern to many people as they age and/or go through body weight changes. Small amounts of fat in the face, neck, and chin can make an otherwise fit person appear to carry more weight than the person actually carries.

Figure 14:
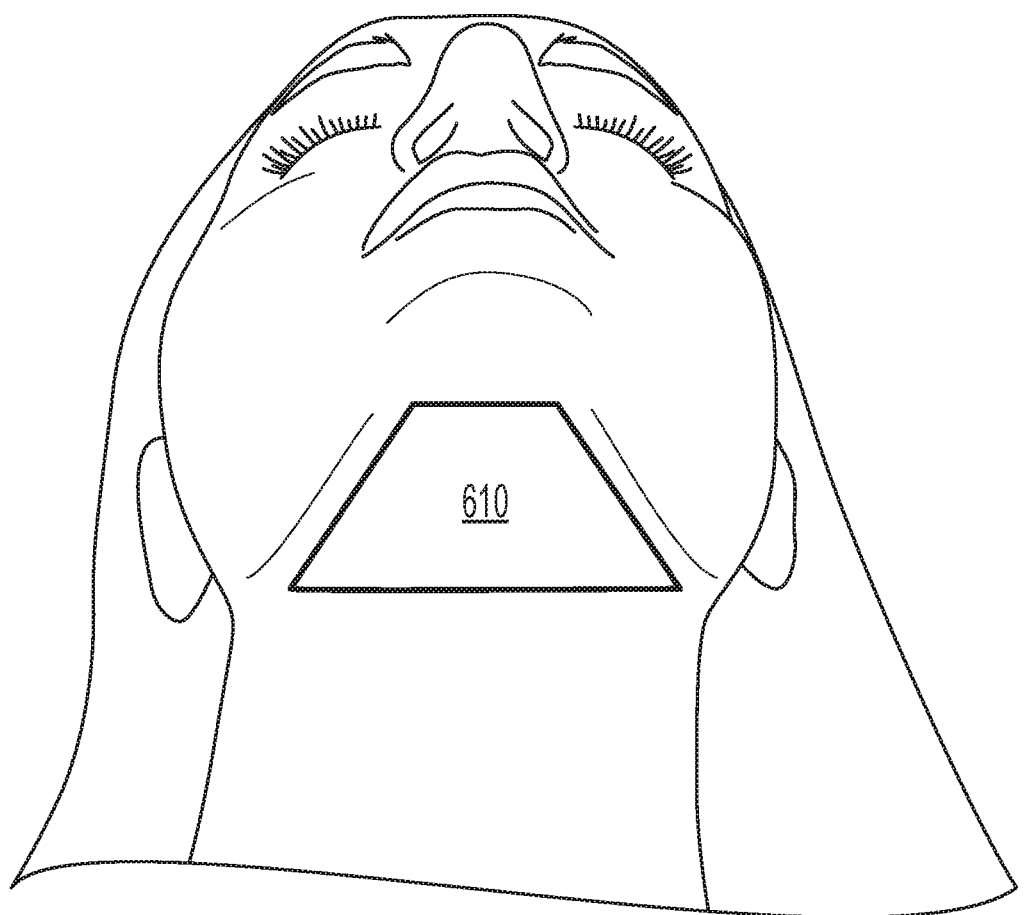
FIG. 14 depicts the submental treatment region.

FIG. 14 depicts the submental treatment region 610 of the face/neck area. The submental treatment region 610 is the region of the lower portion of the face/neck area that is located between the mandible down to the hyoid bone. Fat tissue can localize in the submental region leading to an appearance of submental fullness that a subject finds undesirable. Current treatment options range from liposuction, which is highly invasive, to a non-invasive approach that includes pressing a cooled applicator against the submental region. Other treatment options are desired.

In accordance with various aspects of the present teachings, one or more of the applicators 300 of the system 100 shown in FIG. 1 may be used to treat the undesired fat and fullness in the face, neck, and chin area. In one embodiment, for example, a standard frame 400 of the system 100 can be modified to adjust the irradiation footprint/size of the contact surface of the applicator so as to treat a relatively smaller submental or jowl region with a standard applicator contact surface. In one exemplary embodiment, each standard frame of the system can measure about 4.8 cm by about 9 cm (or about 43.2 cm$^2$) and each contact surface of the applicator can measure about 4 cm by about 6 cm (or about 24 cm$^2$). For example, in some embodiments disclosed herein, a mask portion can be coupled or attached to the frame so as to mask all or a portion of the irradiation footprint of the applicator's skin-contacting surface such that the irradiation surface of the contact surface is reduced (i.e., masked). For example, the mask portion can mask from about 0% to about 80% of the contact surface of the applicator, from about 15% to about 75% of the contact surface of the applicator, from about 25% to about 50% of the contact surface of the applicator, or from about 35% to about 45% of the contact surface of the applicator. In one exemplary embodiment, where the footprint of the applicator contact surface measures 24 cm$^2$, the effective treatment footprint of the contact surface can be reduced to a range from about 23.76 cm$^2$ to about 4.8 cm$^2$ once masked. The mask portion blocks at least a portion of the transmission from the contact surface of the applicator from reaching the subject's tissue. Each mask portion may have a fixed size and shape and multiple masks may be employed depending on the subject's treatment area, for example.

Alternatively, in some aspects, the mask portion can have an adjustable size and/or shape. The mask portion can have any of a number of shapes that may be selected depending on the area to be treated. The mask portion can have a shape that is selected from square, triangular, circular, oval, ellipse, trapezoid, rhombus, pentagon, hexagon, octagon, or parallelogram, for example.

In one exemplary embodiment, the mask portion is the shape of a rectangle that compliments the rectangular shape of the applicator contact surface, but the length of one or both sides of the rectangle is adjustable such that the size of the mask can be increased and the irradiation surface of the applicator contact surface may be reduced. In another embodiment, the mask portion is similar to a photography shutter than can be mechanically altered to increase the area covered by the mask portion to expose less and less of the applicator contact surface such that the irradiation surface is reduced.

Any number of suitable materials may be used to make the mask portion, such as, for example: aluminum, gold plated aluminum, ceramic, silver plated aluminum. In various aspects, it may be desirable to avoid the mask portion from heating up during the treatment of the treatment region. In such aspects, the mask portion can be actively cooled to prevent heat build-up in the mask portion from impacting the subject. Exemplary means for active cooling include, for example, using a thermoelectric cooler, air convection (fan), phase change material (ice), and a separate coolant circuit. Alternatively, the mask portion can be passively cooled, for example, by fins that help move heat away from the region of the mask portion. In such aspects, the fins would have sufficient area and thermal contact to dissipate heat to the surrounding ambient air or the frame of the fixture through conduction or convection. Ideally, the mask and any additional heat it accumulates from the EMR source (e.g., laser) can be wicked away by being in intimate thermal contact with the existing optical window (e.g., sapphire surface) of the applicator, which is being actively cooled.

The one or more applicators can be held adjacent to the subject's face, neck, chin, or head by any of a number of approaches including by: strap/belt, gravity, positioning the patient's body area in a relatively comfortable position relative to the applicator (e.g., applicator placed on a table top and chin placed on top of the applicator). Suitable strap/belt systems used in orthodontia (e.g., head gear) and orthopedics (e.g., neck brace(s)) and modified in accordance with the present teachings may be employed to maintain the applicator's contact surface in desired contact with the area to be treated, for example, for treatment of the face, neck, or chin.

Figure 15A:
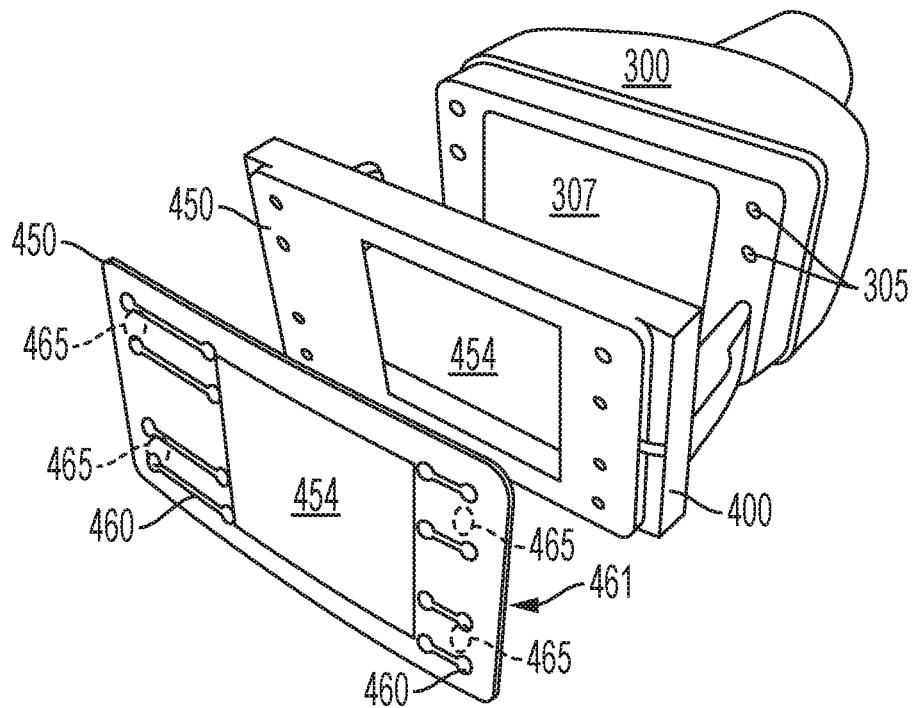
FIGS. 15A-B depict an exemplary applicator/frame/mask sub-assembly for use in the system of FIG. 1, in accordance with various aspects of the present teachings.

With reference now to FIG. 15A, an exemplary sub-assembly is shown with an applicator 300, a frame 400, and a mask portion 450 coupled to the frame 400 and occluding a portion of the frame's aperture 404. The unmasked portion 454 is in the shape a rectangle having a size reduced from the rectangle of the applicator's contact surface 307. Also shown is a contact sensor layer 461 that provides the same masking effect (modifies irradiation in the same size and shape) as the mask portion 450, with the contact sensor layer 461 of the mask enabling the contact sensors 305 of the applicator 300 to be effective in the presence of the mask 450. In this way, the contact detection capability as described above nonetheless remains available when the frame 400 is used in conjunction with the mask portion 450. The contact sensor layer 461 of the mask portion moves or offsets the effective contact sensors 460 to surround the now unmasked portion 454 so that active contact sensing and/or passive contact sensing can be utilized to ensure contact of the surface of the treatment region with the skin-contacting surface 307 exposed by the unmasked portion 454. Any of the uses of a masked portion disclosed herein may likewise employ a contact sensor layer 461 that provides an offset contact sensing capability, via offset contact sensors 460, that enables the contact sensors 305 present in the applicator to nonetheless be effective in the presence of the mask portion 450. The contact sensor layer 461 may optionally include one or more resistors 465 (shown in phantom) disposed between two adjacent effective contact sensors 460. FIG. 15A shows the presence of four resistors 465, though it is not necessary to have a resistor present between each pair of contact sensors. The one or more resistors 465 may be positioned on the side of the effective contact sensors 460 (the skin contacting side) or on the side of the contact sensor layer 461 that is adjacent the applicator surface. The resistor can be employed to provide a signal to the system such that the system will be treating a reduced area due to the presence of a mask 450. As a result of the resistor 465 signal, the treatment parameters may be adjusted in accordance with the reduction in irradiation surface area provided by the unmasked portion 454. Suitable system adjustments that can be made in response to the detection of the presence of a masked portion are, for example, increased cooling to cool the masked portion or reduction of cooling due to lesser surface area being treated. Other parameters that can be adjusted include, for example, the flux and/or the wavelength so as to treat the specific treatment area (e.g., submental area).

Figure 15B:
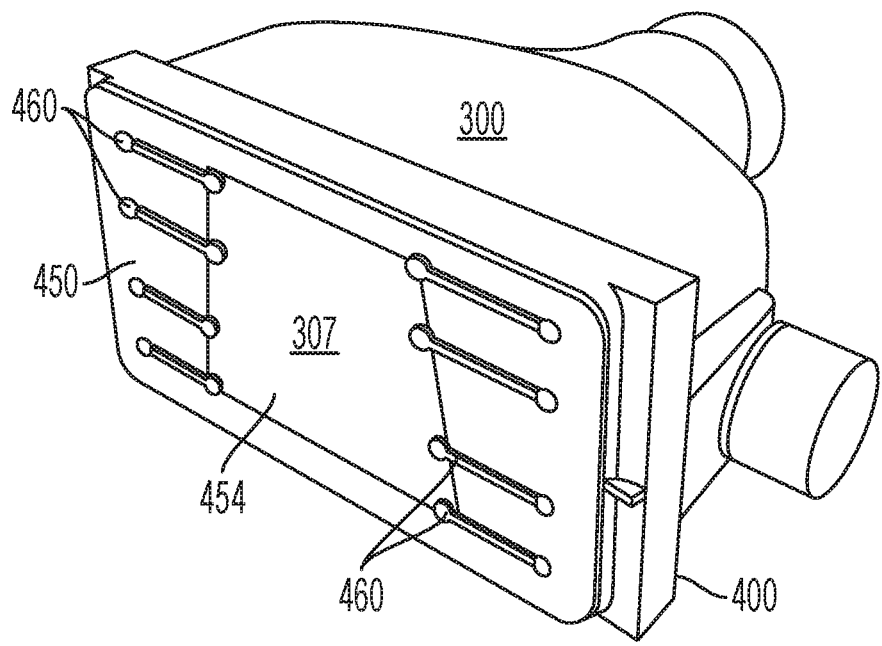

FIG. 15B shows a sub-assembly similar to FIG. 15A but differs in that the mask 450 defines an unmasked portion 454 having the shape of a trapezoid, where the unmasked portion 454 exposes from about 50% to about 80% of the irradiation surface of the applicator skin-contacting surface 307. As shown, the mask 450 includes four pairs (or eight total) of offset contact sensors 460 that effectively extend the applicator contact sensors present on the applicator surface similar to as is shown above in FIG. 15A and labeled 305.

Figures 16A, 16B:
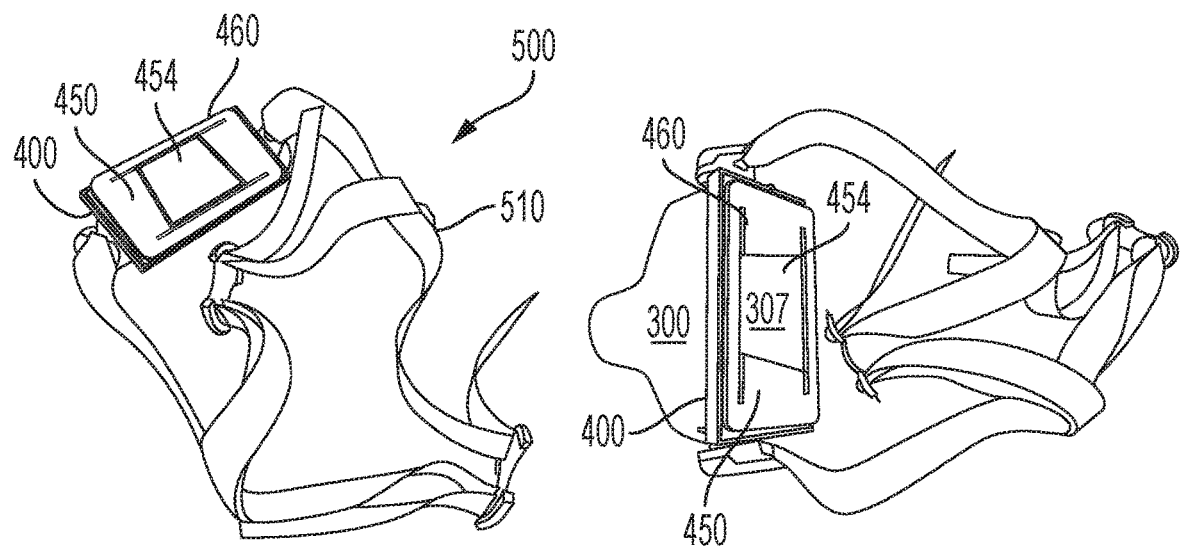
FIGS. 16A-D depict the exemplary applicator/frame/mask sub-assembly of FIGS. 15A-B further coupled to a belt for securing the sub-assembly to the patient's head for treatment of the submental region, in accordance with various aspects of the present teachings.
Figures 16C, 16D:
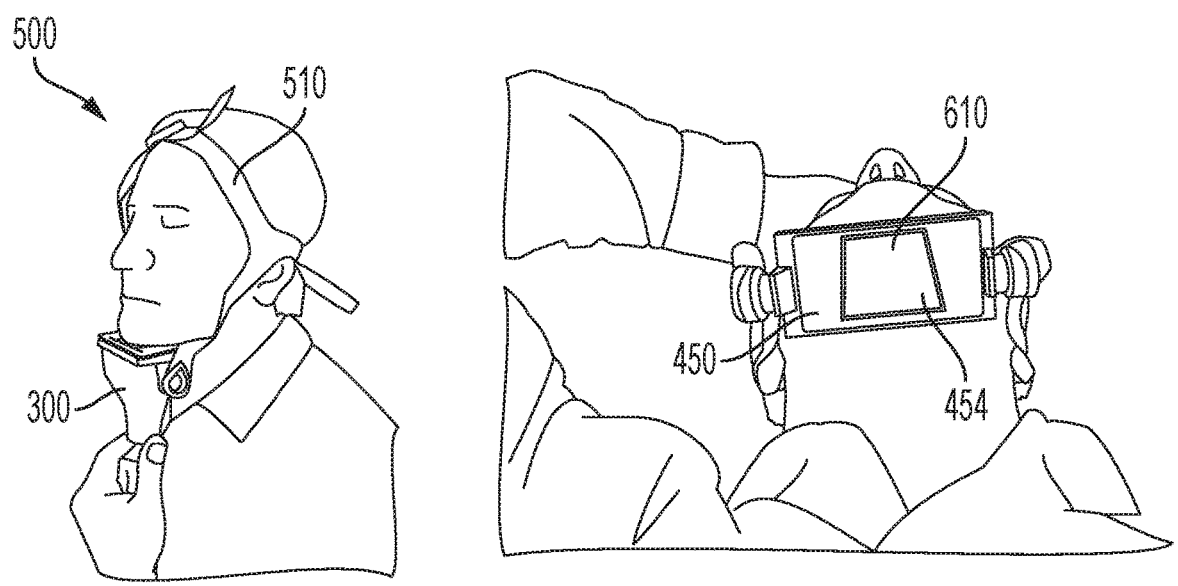

FIG. 16A shows a sub-assembly of frame 400, including a mask 450, having an unmasked portion 454 exposing a trapezoidal shape, with a plurality of offset contact sensors 460 together with a belt system 500, which is similar to a headgear used in orthodontia. FIG. 16B shows an assembly of the applicator 300 coupled with a frame (e.g., snap fit), including a mask 450 that masks all but a trapezoidal portion of the applicator contact surface 307, the unmasked portion 454 having a trapezoidal shape through which a portion of the applicator contact surface 307 is exposed. The assembly also includes one or more offset contact sensors 460, specifically, four offset contact sensors 460, all of which can be secured to the patient with a belt system. In various aspects, the unmasked portion 454 can expose from about 25% to about 80%, or about 50% of the irradiation surface of the applicator's skin-contacting surface 307. It will be appreciated that the amount of masking selected to cover the contact surface can depend, for example, on the shape and/or size of the subject's submental treatment area. FIGS. 16C-D depict the belt system 500 being used to place the masked frame 400 under the chin so as to isolate the submental tissue for treatment 610. As shown in FIG. 16C, the belt system 500 is tightened at the submental/chin region 610 from either end of the frame 400, the belt system 500 traveling up both sides of the jaw line, in front of both of the ears and branching off into a Y shape with one portion strapping around the front of the head 510 in the region of the forehead and the other portion strapping around the region of the back of the head and/or the neck. As best shown in FIG. 16D, the submental region 610 is exposed by the trapezoidal shape of the unmasked portion 454 and thereby treated by the applicator 300 when the skin-contacting surface 307 is in contact with the surface of the submental tissue extending into the trapezoidal shaped unmasked portion 454. In addition to utilizing the belt 500 to secure the frame/mask sub-assembly to the patient as shown in FIG. 16D, the subject of FIG. 16C is depicted as holding the applicator 300 in contact with the submental region 610. It will also be appreciated that in some embodiments, not shown, the subject can be lying down and gravity and/or propped pillows can help to maintain contact between the unmasked skin-contacting surfaces of the applicator and the skin surface. In still other embodiments, the subject can rest his chin against the applicator, which sits at a comfortable height on a table top (or in a construct similar to a slit lamp at an ophthalmologist office), the belt, optionally styled like a headgear used in orthodontia, helping to maintain proper placement of the applicator/frame assembly, with the pressure from the chin rests also helping to ensure good contact. As discussed otherwise herein, the applicator can be connected to the system via an umbilical (not shown).

Figure 17A:
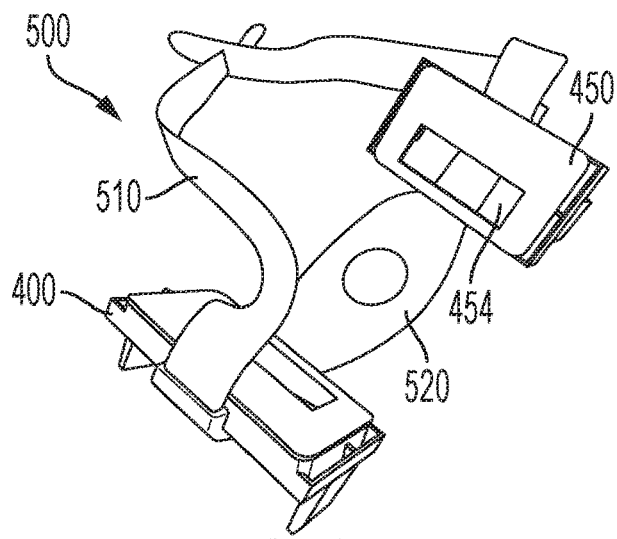
FIGS. 17A-C depict an exemplary sub-assembly having two applicators coupled to two masked frames, together with a belt system for attaching the two frames to one another and to secure the frames to the subject's body for treatment of the jowl's, in accordance with various aspects of the present teachings.
Figure 17B:
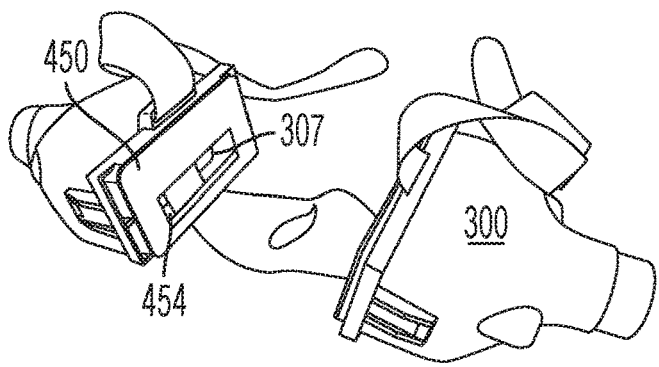
Figure 17C:
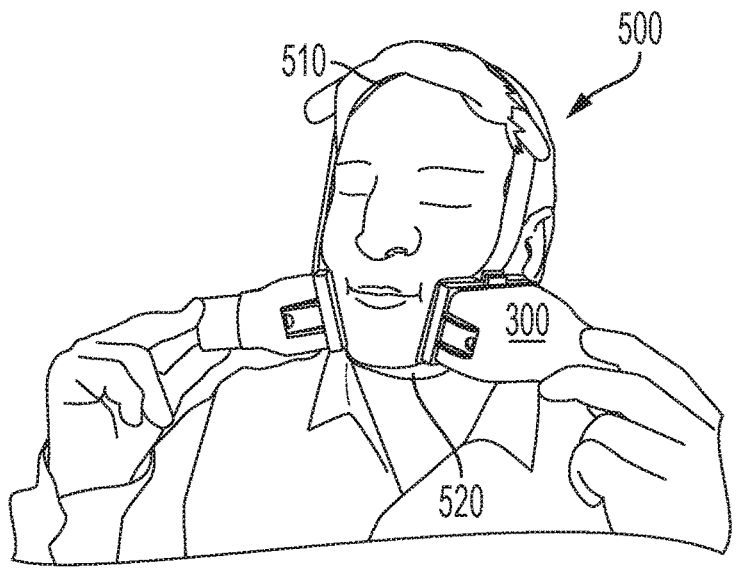

FIG. 17A shows a sub-assembly of two frames 400, each including a mask 450 defining an unmasked portion 454 having a rectangular shape, together with a belt system 500 having a chin strap 520 that attaches to the two frames 400. FIG. 17B depicts the sub-assembly of FIG. 17A with two applicators 300 connected to the frames 400, each frame 400 including an unmasked portion having a rectangular shape 454 surrounded by a masked portion and a belt system that attaches the two frames to one another and can be further joined together by two free ends to encircle and tighten around a subject's body portion. The unmasked rectangular shape 454 exposes a portion of the contact surface 307 of the applicator 300. FIG. 17C shows the sub-assembly shown in FIG. 17B with the two masked applicators each providing an unmasked rectangular portion disposed in contact with the two jowl areas of the face (left hand side and right hand side) above the jawline, with a chin strap 520 portion of the belt 500 between the two frames 400 being secured adjacent the chin, and the two free ends 510 encircling the head and connecting to one another just at the hairline above the forehead. The unmasked portion of each of the frames enables from about 20% to about 50% of the contact surface area of each of the applicators to be in contact with and treat a respective jowl portion. Here, in addition to the belt, the subject is holding the applicators in contact with the jowl area. In another embodiment, not shown, the subject can be lying down, with gravity and/or propped pillows helping to maintain contact between the unmasked contact surfaces of the applicators and the skin surface. As discussed otherwise herein, the applicator can be connected to the system via an umbilical (not shown).

Figure 18A:
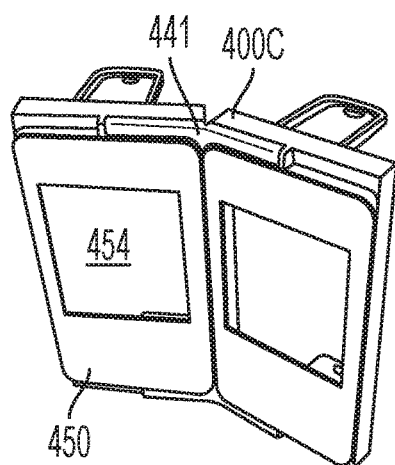
FIGS. 18A-E depict another exemplary sub-assembly having two applicators coupled to a masked frame, each of the applicators being associated with a separate aperture of the frame, and a belt system for securing the frame to the subject's body for treatment of the submental region, in accordance with various aspects of the present teachings.
Figure 18B:
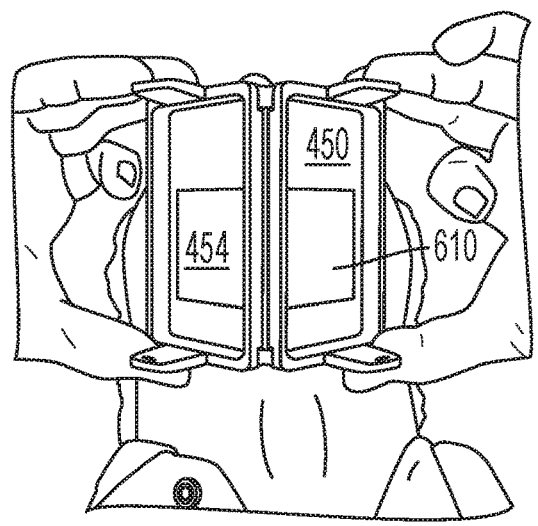
Figure 18C:
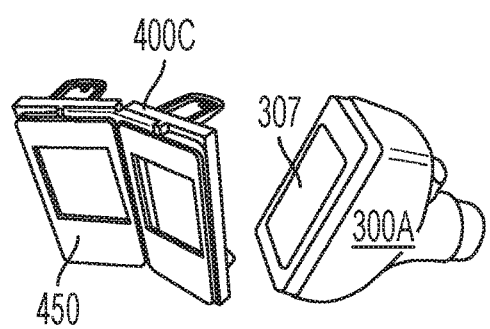
Figure 18D:
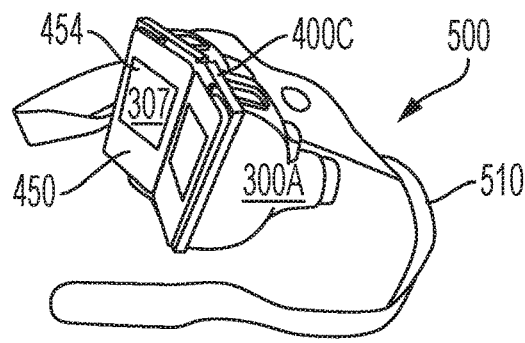
Figure 18E:
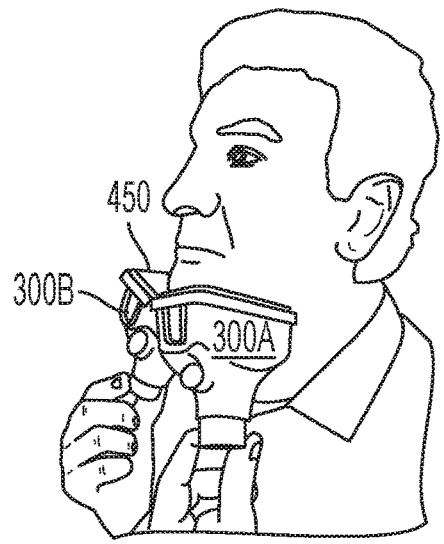

With reference now to FIGS. 18A-E, the sub-assembly includes two frames 400C (shown also in FIG. 8), with each frame 400C being coupled to a mask 450, where the unmasked portions 454 have a rectangular shape. The two frames 400C are connected to one another by a hinge 441. FIG. 18B shows the two masked hinged frames of FIG. 18A being held against the submental region 610, where the unmasked portions 454 reveal a left hand side and the right hand side of the submental region 610 with each side being isolated for tissue treatment by the unmasked portion 454 of the frame 400. The unmasked portion 454 enables irradiation from about 40% to about 75% of each of the applicator contact surfaces 307 to be delivered to the respective treatment areas (see FIG. 18C). FIG. 18C shows the two masked hinged frames of FIG. 18A together with an applicator 300A. FIG. 18D shows the two masked hinged frames of FIG. 18A snap fit attached to two applicators, revealing a substantially rectangular portion of the applicators' contact surfaces 307 through the unmasked portion 454 unobstructed by the mask 450. As discussed above, a belt 500 can also be attached to the frames 400C and can be used to secure the applicators 300 together with the frames about a portion of a subject's body (e.g., to surround the subject's head). FIG. 18E shows an assembly of two applicators 300A, 300B snap fit to the two masked hinged frames 400C of FIGS. 18A-D in contact with the submental region 610 of a subject. Here, the subject is holding the assemblies in contact with the submental region 610, though additionally or alternatively, the belt 500 shown in FIG. 18D may be used to secure the applicators to the submental region by encircling the belt around the head. In still another embodiment as otherwise discussed herein, the subject can rest his chin against the applicators, which can sit at a comfortable height on a table top, for example. As discussed above, the applicator can be connected to the system via an umbilical (not shown).

Figure 19A:
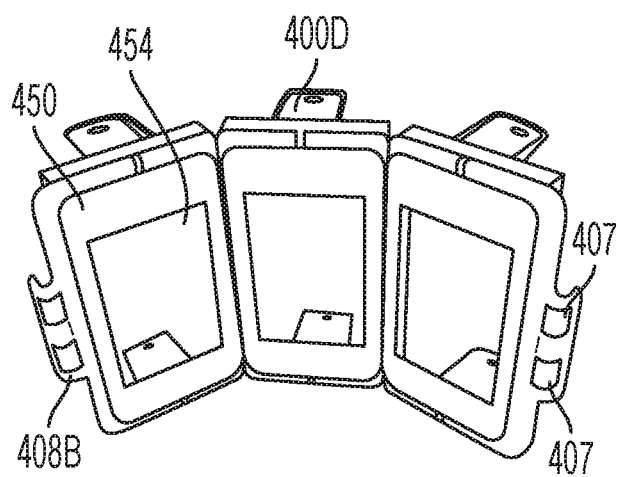
FIGS. 19A-D depict another exemplary sub-assembly having two applicators coupled to a masked, hinged frame, each of the applicators being associated with a separate aperture of the frame (with the middle aperture not being associated with an applicator), and a belt system for securing the frame to the subject's body for treatment of the neck region, in accordance with various aspects of the present teachings.
Figure 19B:
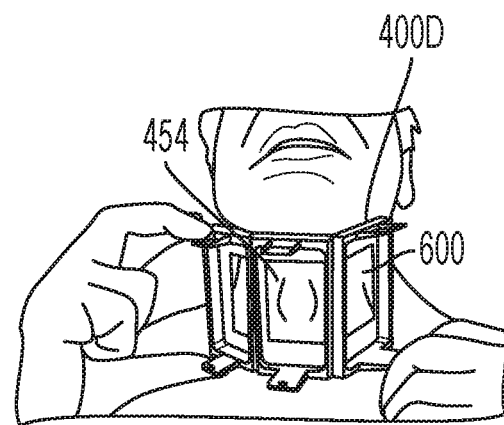
Figure 19C:
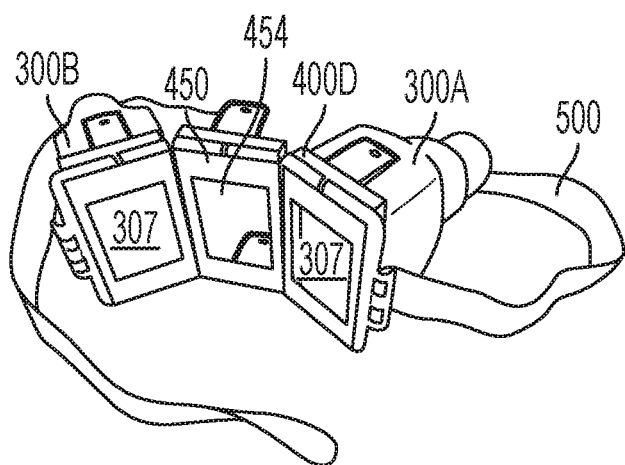

With reference now to FIGS. 19A-C, a hinged frame 400D defining three apertures 404 is coupled to a mask 450 defining three unmasked portions 454 having a rectangular shape. Tabs 408B include multiple belt loops 407 on either side of the frame 400D and enable the frame to be angled by using, for example, an upper belt loop on the left side and a lower belt loop on the right side. Though two belt loops 407 are shown on either side, it will be appreciated that a frame could employ any of a number of belt loops 407 so that the desired angling or positioning of the frame on the body can be achieved. For example, where six loops are present on a frame on the left side, the top loop can be used and on the right side the bottom loop can be used, this way desired positioning can be achieved for any of a number of body areas, not limited to the neck area, as shown here. In one embodiment, there is one belt loop on two sides of a frame. In another embodiment, more than one belt loop can be present on two sides of the frame.

Figure 19D:
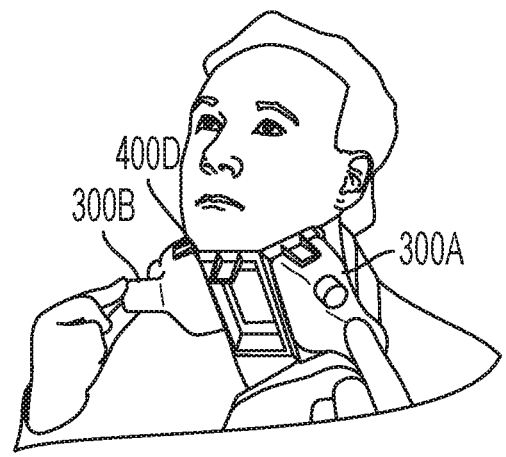

FIG. 19B shows the three masked hinged frames 400D of FIG. 19A held against the neck region, where the unmasked portion 454 reveal three portions of the neck region 600 that are isolated for tissue treatment. FIG. 19C shows the three masked, hinged frames of FIG. 19A snap fit attached to two applicators 300A, 300B revealing a substantially rectangular shaped contact surface 307 of each applicator through the unmasked portion 454 of two of the apertures of the frame 400D, with the center masked frame 400D not being attached to an applicator. As shown, a belt 500 is attached to the frame 400D to secure the applicators about a portion of a subject's body (e.g., about a subject's head). FIG. 19D shows an assembly of two applicators 300A and 300B snap fit to the frame 400D and associated with two of the three apertures as shown in FIGS. 19A-C, the attached applicators being in contact with the neck region, with the subject holding the two applicators 300A, 300B in contact with the neck region. In another embodiment, not shown, the belt 510 can be used to secure the applicators 300A, 300B and their masked frames 400D against the neck region by encircling the back of the neck. As discussed otherwise herein, the applicator can be connected to the system via an umbilical (not shown).

Figure 20A:
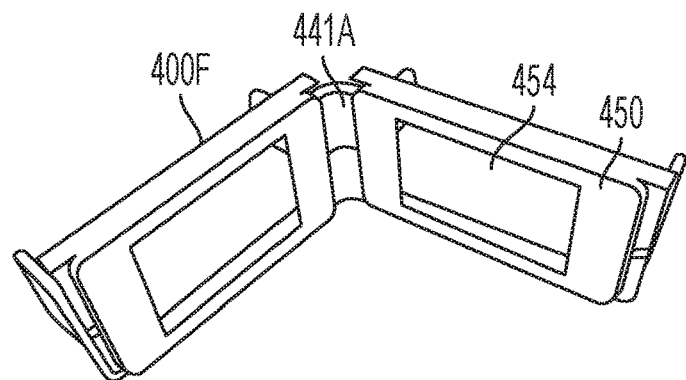
FIGS. 20A-C depict another exemplary sub-assembly for treating the neck region in accordance with various aspects of the present teachings, the sub-assembly having two applicators coupled to a masked, hinged frame, each of the applicators being associated with a separate aperture of the frame, and a belt system for securing the frame to the subject's body.
Figure 20B:
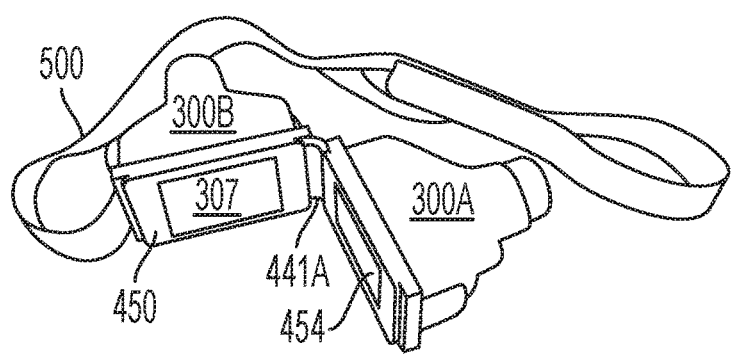
Figure 20C:
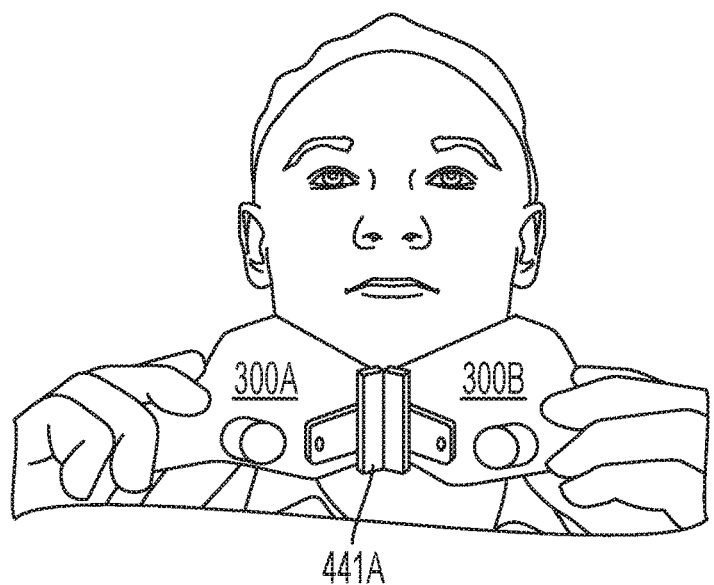

With reference now to FIGS. 20A-C, a masked frame 400F is depicted in which the unmasked portion 454 of the apertures of the frames 400F have a rectangular shape. The frames 400F are hinged 441A on their short side. FIG. 20B shows the masked, hinged frame 400F of FIG. 20A snap fit attached to the two applicators 300A, 300B, revealing a substantially rectangular portion of applicators' skin-contacting surface 307 through the unmasked portion 454. As shown, a belt 500 is also attached to the frame 400F and can be used to secure the applicators about a portion of a subject's body, e.g., about the face or neck. FIG. 20C shows the assembly of two applicators 300A, 300B, snap fit to rectangular the frame 400D that is hinged 441A on the short side, the unmasked portion 454 of the contact surface (shown in FIG. 20B) in contact with the neck region of a subject, with the subject holding the assemblies in contact with the neck region under the jawline. In another embodiment, not shown, the belt 500 can be used to secure the applicators against the neck region by encircling the back of the neck. In still another embodiment, the subject can be lying down on his back and the force of gravity, optionally together with propped pillows, can also help maintain contact between the unmasked portions of the applicator contact surface and the treatment area. As discussed otherwise herein, the applicator can be connected to the system via an umbilical (not shown).

Figure 21A:
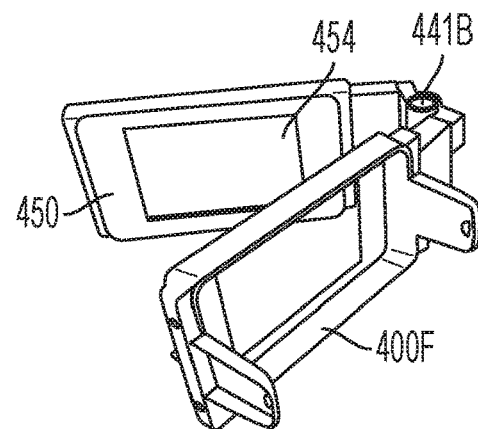
FIGS. 21A-C depict another exemplary sub-assembly for treating the neck region in accordance with various aspects of the present teachings, the sub-assembly having two applicators coupled to a masked, hinged frame, each of the applicators being associated with a separate aperture of the frame, and a belt system for securing the frame to the subject's body.
Figure 21B:
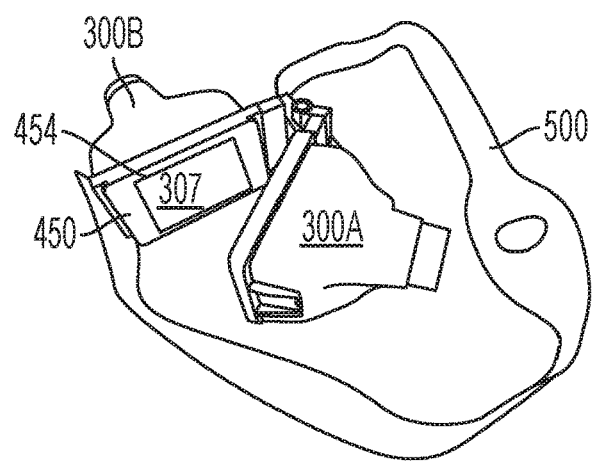
Figure 21C:
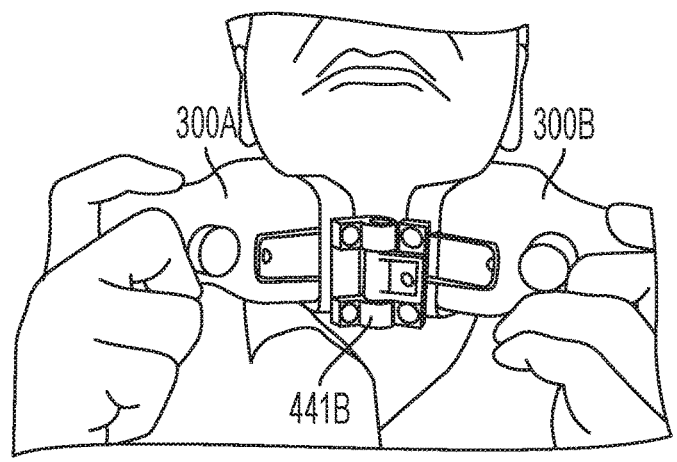

FIGS. 21A-C shows two masked frames 400F, where the unmasked portion 454 of the frame apertures 404 have a rectangular shape. The frames 400F are hinged 441B on their short side. The hinges 441B depicted in FIGS. 21A-C offer a greater range of motion and adjustability relative to the hinges 441A shown in FIGS. 20A-C, which can enable treatment of different areas and/or subjects having more fullness in the neck region. FIG. 21B shows the two masked, hinged frame 400F of FIG. 21A snap fit attached to the two applicators 300A, 300B revealing a substantially rectangular shaped surface of each applicator's skin contact surface 307 through the unmasked portion 454 of the mask 450. The unmasked portion 454 reveals from about 60% to about 80% of the available contact surface 307 of the applicator 300A, 300B. A belt 500 is attached to the frames 400F and can be used to secure the applicators together with the masked frames about a portion of a subject's body. FIG. 21C shows an assembly of two applicators 300A,B snap fit to the frame 400F of FIGS. 21A and 21B, with the skin-contacting surface 307 of the applicator being in contact with the isolated a portion of the isolated treatment region extending through the apertures 404 of the frame, with the subject holding the assemblies in contact with the neck region under the jawline. In another embodiment, not shown, the belt 500 can be used to secure the applicators against the neck region by encircling the back of the neck. In still another embodiment, the subject can be lying down on his back and the force of gravity, optionally together with propped pillows, can also help maintain contact between the unmasked portions of the applicator contact surface and the treatment area. As discussed otherwise herein, the applicator can be connected to the system via an umbilical (not shown).

Figure 22A:
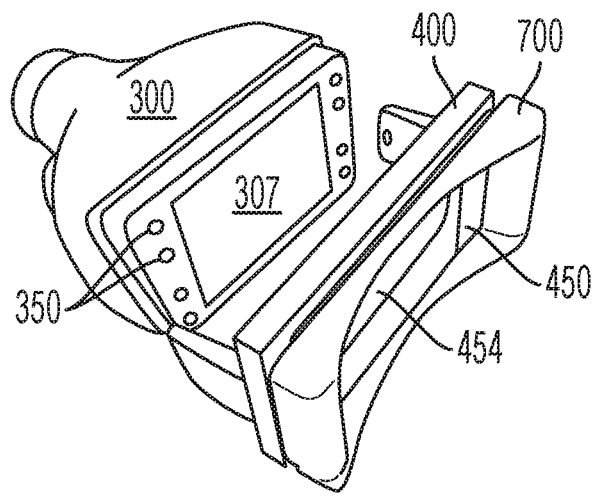
FIG. 22A-C depict another exemplary applicator/frame/mask sub-assembly for use in the system of FIG. 1 in which the skin-contacting surface of the frame is contoured (non-planar) to improve patient comfort during treatment of the submental region in accordance with various aspects of the present teachings.
Figure 22B:
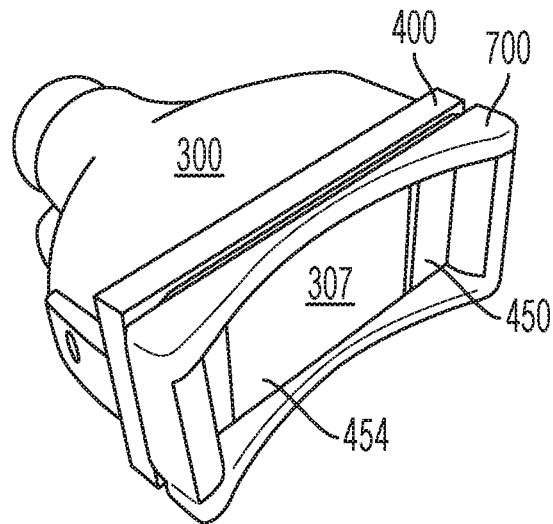
Figure 22C:
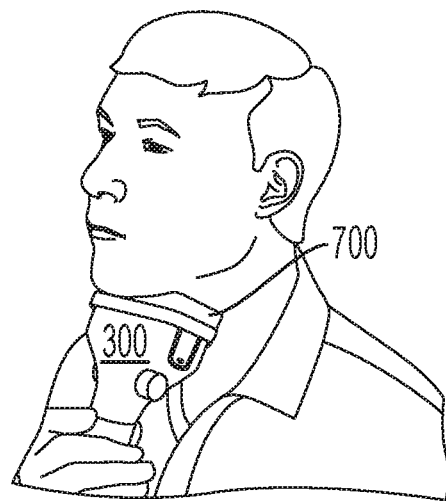

With reference now to FIGS. 22A-C, an applicator 300, a frame 400 including a mask 450 defining an unmasked portion 454, and a non-planar, contoured skin-contacting portion 700 is depicted. FIG. 22B shows the assembly of the applicator 300 attached to the frame 400, the mask 450 (defining the unmasked portion 454) and the contoured portion 700. FIG. 22C shows the sub-assembly of the applicator 300 removably attached to the masked frame 400, with the contoured portion 700 being held adjacent the submental treatment by the subject's hand. It will be appreciated that just as the contoured portion 700 can be shaped so as to form fit the submental convex region, other shapes are possible to match the contour of the treatment region. In some aspects, the contoured portion can limit the amount of contact enabled between the submental region and the applicator contact surface. In this way, a mask can, in some embodiments, be avoided. Rather, the access provided by the contoured portion can limit the effective irradiation surface of the contact surface 307 of the applicator 300.

In another embodiment, not shown, the subject can be lying down with gravity and/or propped pillows helping to maintain contact between the unmasked contact surfaces of the applicator and the skin surface. In still another embodiment, the subject can rest his chin against the applicator, which can sit at a comfortable height on a table top, for example, with the pressure from the chin resting against the applicator helping to ensure good contact for treatment. Optionally, a belt (not shown) from either side of the frame can encircle the subject's head to help maintain proper placement of the applicator/frame assembly, with the pressure from the chin rest also helping ensure good contact. In some embodiments, a contact sensor that may be offset from the applicator contact sensor can be coupled to the frame and/or the contoured portion 700 of the frame. As discussed otherwise herein, the applicator can be connected to the system via an umbilical (not shown).

Figure 23:
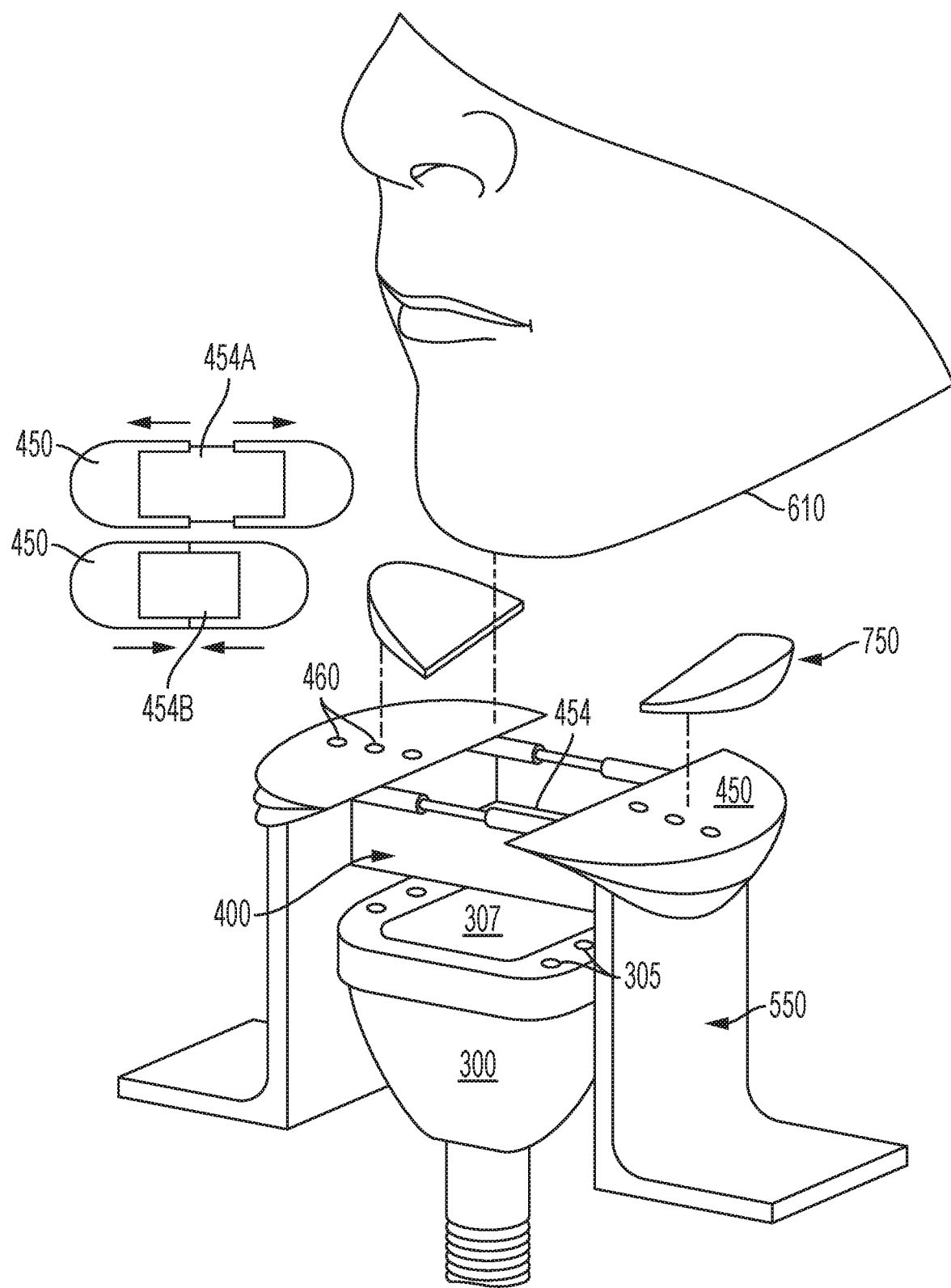
FIG. 23 schematically depicts another exemplary applicator/frame/mask sub-assembly in accordance with various aspects of the present teachings for treatment of the submental region

With reference now to FIG. 23, an exemplary table top stand 550 is depicted having an adjustable mask 450 positioned thereon. The table-top stand 550 (e.g., similar to a slitlamp used in ophthalmology) can be positioned at a height comfortable to the subject. As shown, an applicator 300 can be positioned under a frame 400 on top of which sits the masked portion 450. As otherwise discussed herein, the applicator 300 can connect to the table top 550 stand via a coupling with frame 400 (e.g., a snap fit). As shown in inset, the size of the mask 450 can be adjustable to provide a relatively larger unmasked portion 454A or a relatively smaller unmasked portion 454B, thereby exposing more or less of the applicator contact surface 307 as desired. The adjustment of the masked portion relative to the unmasked portion can be adjusted depending, for example, on the size of the submental region of the subject to be treated.

As shown in FIG. 23, the subject can rest his submental area 610 on the adjusted mask portion 450 for treatment of the portion that remains unmasked 454. Optionally, chin rests 750 can be placed between the mask 450 and the subject's chin to ensure good positioning of the submental area on the skin-contacting surface 307. Optionally, the adjustable mask and/or the chin rests can include contact sensors (e.g., such as offset contact sensors 460 described above) that extend the effectiveness of the contact sensors 305 to ensure contact of the treatment region of with the contact surface 307 exposed by the unmasked portion 454. In some embodiments, the mask and/or the chin rests can provide a heat sink to ensure that the masked area is comfortable to the subject.

The systems of treatment of the face, neck, chin, and jaw disclosed herein may use the exemplary system 100 disclosed in association with FIG. 1. In some embodiments, one or more umbilical cords 405 may be temporarily freed or removed from the arm 420 and the brake mechanism 410 to enable a greater range of motion of the applicator(s) 300 and the umbilical cord(s) 400 for treatment in accordance with any of the applications disclosed in association with FIGS. 14-23.

The systems and methods disclosed herein is discussed in relation to treatment of body areas having undesired fat and bulges. The disclosed system and method of treatment of external treatment of the body of a subject may applied to other treatment modalities that are external to the body (e.g., non-invasive) such as, for example, pain treatment, acne treatment, wound treatment, skin rejuvenation, and/or skin tightening.

In one aspect, this disclosure relates to a system for substantially unattended treatment including a frame encircling at least portion of a circumference of a body region. The frame has at least one aperture sized to isolate at least one portion of a body region and the frame has a first fastening member. The system also includes an applicator having a skin contacting surface. The applicator has a second fastening member that detachably fastens with the first fastening member when the applicator is inserted into the frame. In one embodiment, the first fastening member and the second fastening member include a male member and a female member that snap fit. In one embodiment, at least two frames of a plurality of frames are attached to one another by a hinge.

The system can include a belt and the frame is removably attached to the belt. All or a portion of the belt may be flexible. All or a portion of the belt can encircle the portion of the circumference of the body region.

In one embodiment, the applicator emits hyperthermic energy through the skin contacting surface.

In one aspect, this disclosure relates to a system for substantially unattended treatment including a frame encircling at least portion of a circumference of a body region. The frame has at least one aperture sized to isolate at least one portion of a body region and the frame has a first fastening member. The system also includes an applicator having a skin contacting surface. The applicator has a second fastening member that detachably fastens with the first fastening member when the applicator is inserted into the frame. In one embodiment, the umbilical cord has a first end coupled to an energy source and a second end coupled to the applicator. In some embodiments, the system includes an arm having a braking mechanism. A portion of the umbilical cord between the two ends is threaded through the breaking mechanism and the breaking mechanism holds a portion of the umbilical cord selected by the user so that the position of umbilical cord that lies between the breaking mechanism and the applicator enables the desired contact between the applicator skin contact surface and the portion of the body.

In another aspect, the disclosure relates to methods of treatment of a body region using a frame having at least one aperture to isolate a body region and then bringing the contact surface of an applicator in contact with the body region by fastening the applicator to the frame and treating the body region for any of a number conditions such as unwanted fat bulges, acne, pain, wound healing, and loose skin via this non-invasive approach.

While the foregoing figures and examples refer to specific elements, this is intended to be by way of example and illustration only and not by way of limitation. It should be appreciated by the person skilled in the art that various changes can be made in form and details to the disclosed embodiments without departing from the scope of the teachings encompassed by the appended claims.

The invention claimed is:

1. A method of treating body tissue using a non-invasive body contouring system, comprising:
providing a first frame comprising a first fastening member, the first frame defining a first aperture;
coupling the first frame to a patient's body in a fixed position relative to a tissue treatment region such that a surface of the tissue treatment region extends into the first aperture;
coupling a first applicator to the first frame, using the first fastening member, the first applicator comprising an optical window having a skin-contacting surface;
contacting a portion of the surface of the tissue treatment region extending into the first aperture with the skin-contacting surface of the optical window upon coupling the first applicator to the first frame;
generating treatment energy from a source disposed in a housing of the non-invasive body contouring system;
delivering the treatment energy to the first applicator via an umbilical extending from the housing to the first applicator; and
transmitting the treatment energy delivered to the first applicator through the first aperture.

2. The method of claim 1 further comprising
providing a second frame comprising a second fastening member, the second frame defining a second aperture;
coupling the second frame to the patient's body; and
coupling a second applicator to the second frame using the second fastening member.

3. The method of claim 2, wherein the first frame and the second frame are linked by a hinge disposed between the first aperture and the second aperture, wherein coupling the first frame and the second frame to the patient's body further comprises adjusting orientation of the first aperture and the second aperture relative to each other.

4. The method of claim 1, wherein the housing comprises at least one arm extending from the housing for supporting the umbilical cord, the method further comprising disposing the arm above the patient's body when performing treatment.

5. The method of claim 4, wherein the arm comprises at least one brake in contact with the umbilical so as to maintain a desired amount of lead of the umbilical cord between the at least one brake and the applicator associated with the umbilical.

6. The method of claim 1, wherein coupling the first frame to the patient's body comprises securing a belt coupled to the first frame around at least a portion of the patient's body.

7. The method of claim 6, wherein the treatment region comprises one of submental, jowl, and neck tissue and wherein the belt is secured about the patient's head or neck.

8. The method of claim 6, wherein the treatment region comprises abdominal tissue, and wherein the belt is secured about the patient's torso.

9. The method of claim 6, wherein the treatment region comprises tissue of the patient's arm or leg, and wherein the belt is secured around the patient's arm or leg, respectively.

10. The method of claim 1, further comprising coupling the frame to at least one mask configured to occlude a portion of the aperture of the frame so as to prevent a portion of the surface of the patient's body from extending into the first aperture and into contact with the optical window of the first applicator.

11. The method of claim 10, wherein the mask defines an unmasked portion having an area smaller than the optical window of the first applicator and the first aperture of the first frame associated with the mask, the method further comprising adjusting at least one of the size and shape of the unmasked portion.

12. The method of claim 1, wherein the skin surface extends into the first aperture in response to coupling the first frame to the patient's body.

13. A method of treating body tissue using a non-invasive body contouring system, comprising:
providing a first frame and a second frame, wherein the first frame and the second frame are connected, the first frame comprising a first fastening member, the first frame defining a first aperture, the second frame comprising a second fastening member, the second frame defining a second aperture;
coupling the connected first frame and second frame to a patient's body in a fixed position such that a first tissue treatment region extends into the first aperture and a second tissue treatment region extends into the second aperture;
coupling a first applicator to the first frame, using the first fastening member;
coupling a second applicator to the second frame, using the second fastening member;
generating treatment energy from a source disposed in a housing of the non-invasive body contouring system;
delivering the treatment energy to the first applicator via a first umbilical extending from the housing to the first applicator; and
delivering the treatment energy to the second applicator via a second umbilical extending from the housing to the second applicator.

* * * * *